US012291745B2

(12) United States Patent
Phillips et al.

(10) Patent No.: US 12,291,745 B2
(45) Date of Patent: May 6, 2025

(54) METHODS AND SYSTEMS FOR VALIDATION OF A NUCLEIC ACID AMPLIFICATION ASSAY

(71) Applicant: BIOFIRE DEFENSE, LLC, Salt Lake City, UT (US)

(72) Inventors: Cynthia L. Phillips, Salt Lake City, UT (US); Kenneth K. C. Bramwell, Salt Lake City, UT (US); Kirk M. Ririe, Salt Lake City, UT (US); Mark Aaron Poritz, Salt Lake City, UT (US)

(73) Assignee: Biofire Defense, LLC, Salt Lake City, UT (US)

( * ) Notice: Subject to any disclaimer, the term of this patent is extended or adjusted under 35 U.S.C. 154(b) by 1267 days.

(21) Appl. No.: 16/965,853

(22) PCT Filed: Jan. 29, 2019

(86) PCT No.: PCT/US2019/015510
§ 371 (c)(1),
(2) Date: Jul. 29, 2020

(87) PCT Pub. No.: WO2019/152336
PCT Pub. Date: Aug. 8, 2019

(65) Prior Publication Data
US 2023/0159998 A1 May 25, 2023

Related U.S. Application Data

(60) Provisional application No. 62/623,802, filed on Jan. 30, 2018.

(51) Int. Cl.
*C12Q 1/68* (2018.01)
*B01L 3/00* (2006.01)
*B01L 7/00* (2006.01)
*C12Q 1/686* (2018.01)

(52) U.S. Cl.
CPC ........ *C12Q 1/686* (2013.01); *B01L 3/502715* (2013.01); *B01L 7/52* (2013.01); *B01L 2200/16* (2013.01); *B01L 2300/0654* (2013.01); *B01L 2300/0861* (2013.01); *B01L 2300/18* (2013.01); *B01L 2400/0481* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS 6,605,451 B1* 8/2003 Marmaro ............ C12Q 1/6844 435/6.12
9,834,815 B2 12/2017 Brewer et al.
2016/0032366 A1* 2/2016 Mustapha ............. C12Q 1/689 435/6.12
2016/0281182 A1* 9/2016 Monpoeho ........... C12Q 1/6876
2016/0323266 A1* 11/2016 Blöcher ................ H04L 63/101
2023/0159998 A1* 5/2023 Phillips ............. B01L 3/502715 435/6.12

FOREIGN PATENT DOCUMENTS

| | | | |
|---|---|---|---|
| WO | WO2000/066777 | 11/2000 | |
| WO | WO2013/074391 | 5/2013 | |
| WO | WO-2013074391 A1 * | 5/2013 | ............ A61J 1/1425 |
| WO | WO2015/155723 | 10/2015 | |
| WO | WO-2015155723 A1 * | 10/2015 | ........... C12Q 1/6806 |
| WO | WO-2019152336 A1 * | 8/2019 | ........ B01L 3/502715 |

OTHER PUBLICATIONS

Babady et al., 2013. The FilmArray® respiratory panel: an automated, broadly multiplexed molecular test for the rapid and accurate detection of respiratory pathogens. Expert review of molecular diagnostics, 13(8), pp. 779-788. (Year: 2013).*
Bouzid et al., 2021. Rapid diagnostic tests for infectious diseases in the emergency department. Clinical microbiology and infection, 27(2), pp. 182-191. (Year: 2021).*
Burggraf et al., 2004. Simple technique for internal control of real-time amplification assays. Clinical chemistry, 50(5), pp. 819-825. (Year: 2004).*
Chan et al., 2016. Detection of Dientamoeba fragilis in animal faeces using species specific real time PCR assay. Veterinary Parasitology, 227, pp. 42-47. (Year: 2016).*
Czilwik et al., 2015. Rapid and fully automated bacterial pathogen detection on a centrifugal-microfluidic LabDisk using highly sensitive nested PCR with integrated sample preparation. Lab on a Chip, 15(18), pp. 3749-3759. (Year: 2015).*
Gadsby et al., 2015. Development of two real-time multiplex PCR assays for the detection and quantification of eight key bacterial pathogens in lower respiratory tract infections. Clinical microbiology and infection, 21(8), 788-e1, pp. 1-13. (Year: 2015).*
Grape et al., 2007. Standard and real-time multiplex PCR methods for detection of trimethoprim resistance dfr genes in large collections of bacteria. Clinical Microbiology and Infection, 13(11), pp. 1112-1118. (Year: 2007).*
Hobson-Peters et al., 2007. Development of an internally controlled, homogeneous polymerase chain reaction assay for the simultaneous detection and discrimination of herpes simplex virus types 1 and 2 and varicella-zoster virus. Molecular and cellular probes, 21(1), pp. 24-30. (Year: 2007).*
Li et al., 2012. The development of a GeXP-based multiplex reverse transcription-PCR assay for simultaneous detection of sixteen human respiratory virus types/subtypes. BMC Infectious Diseases, 12(1), pp. 1-8. (Year: 2012).*
Ni et al., 2012. Development and utility of an internal threshold control (ITC) real-time PCR assay for exogenous DNA detection. PLoS One, 7(5), p. e36461. (Year: 2012).*
(Continued)

*Primary Examiner* — Stephanie K Mummert
*Assistant Examiner* — Olayinka A Oyeyemi
(74) *Attorney, Agent, or Firm* — Barnes & Thornburg LLP

(57) ABSTRACT

Systems, methods, and apparatus are provided for external control testing of an assay system.

12 Claims, 11 Drawing Sheets

(56) References Cited

OTHER PUBLICATIONS

Poritz et al., 2011. FilmArray, an automated nested multiplex PCR system for multi-pathogen detection: development and application to respiratory tract infection. PloS one, 6(10), p. e26047. (Year: 2011).*
Van Doorn et al., 2009. Accurate quantification of microorganisms in PCR-inhibiting environmental DNA extracts by a novel internal amplification control approach using Biotrove OpenArrays. Applied and Environmental Microbiology, 75(22), pp. 7253-7260. (Year: 2009).*
Ekstrom et al., 2015. Automated amplicon design suitable for analysis of DNA variants by melting techniques. BMC Research Notes, 8(1), pp. 1-11. (Year: 2015).*
Maaroufi, 2006. Development of a multiple internal control for clinical diagnostic real-time amplification assays. FEMS Immunology & Medical Microbiology, 48(2), pp. 183-191. (Year: 2006).*
Genbank Accession No. NC_038882.1—Hepatitis C virus (isolate H77) genotype 1, complete cds, submitted Jul. 1, 1997, retrieved on Aug. 6, 2024 from http://www.ncbi.nlm.nih.gov/nuccore/NC_038882.1). (Year: 1997).*
PCT Search Report and Written Opinion prepared for PCT/US2019/015510, completed Mar. 12, 2019.

* cited by examiner

METHODS AND SYSTEMS FOR VALIDATION OF A NUCLEIC ACID AMPLIFICATION ASSAY

RELATED APPLICATIONS

This application is a national stage entry under 35 U.S.C. § 371 of the PCT International Application Number PCT/US2019/015510, filed 29 Jan. 2019, which claims the benefit of and priority to U.S. Prov. App. Ser. No. U.S. 62/623,802 filed 30 Jan. 2018, the entirety of both of which are incorporated by reference herein.

GOVERNMENT INTEREST

This invention was made with government support under HHSN272201600002C awarded by the U.S. National Institutes of Health and W911QY-13-D-0080 awarded by the U.S. Department of Defense. The government has certain rights in the invention.

BACKGROUND

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest diseases caused by some pathogens and eliminate others as the etiological agent, a variety of potential causative agents remain, and clear diagnosis often requires a variety of assays be performed. Traditional microbiology techniques for identifying pathogens in clinical specimens can take days or weeks, often delaying a proper course of treatment.

In recent years, the polymerase chain reaction (PCR) has become a method of choice for rapid identification of infectious agents. PCR can be a rapid, sensitive, and specific tool to diagnose infectious disease. However, a challenge to using PCR as a primary means of diagnosis is the variety of possible causative organisms or viruses and the low levels of organism or virus present in some pathological specimens. It is often impractical to run large panels of PCR assays, one for each possible causative organism or virus, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, UT) reduce handling, thereby diminishing contamination risk.

Quality control ('QC') materials are necessary to ensure proper performance of an in vitro diagnostic ('IVD') system. For instance, QC material is run on FilmArray assay pouches at the time of manufacture to confirm that the pouches were manufactured according to specification and to confirm that the assays and instruments are operating correctly. Clinical Laboratories in the United States are required under the Clinical Laboratory Improvement Amendments of 1988 (CLIA) to run what is referred to as external control material ('ECM'), which are assay positives and negatives, on each lot of assays received to ensure that the IVD assays in each lot are performing according to specification and to make sure that the lab's procedures are correct for detection of the organisms intended to be detected by the IVD assays. ECMs are also used to verify assay performance on new or repaired instruments, and with new users. In most cases, clinical laboratories have used well-characterized positive clinical specimens or live pathogens spiked into known negative specimens. For especially pathogenic organisms, inactivated organisms may be used to formulate ECMs. In lower complexity laboratories (such as physician-office laboratories) or for assays of rare or highly pathogenic organisms, synthetic nucleic acid template may also be used as ECMs. Non-clinical laboratories in many other industries also run control materials such as ECMs.

Technical Problems

One of the problems with this approach, however, is that organism and nucleic acid positive controls have the potential to contaminate future assays and produce false positives. After amplification, a PCR reaction mix may contain as many as $10^{11}$ to $10^{12}$ copies of the original target. Given the desirability that PCR-based assays for infectious pathogens be sensitive to <50 copies of the target sequence, this means that ~$10^{-8}$ μL (roughly, a billionth of a drop) of the post-amplification mix contains sufficient target to contaminate a subsequent amplification process and cause a false-positive result. Avoiding such carryover contamination, or rendering it harmless, is a difficult challenge.

False positive results from product carryover have plagued PCR assays for many years, and several possible solutions to this problem have been proposed and developed, e.g., observation of strict protocols, enzymatic or chemical treatment of PCR products to render them unamplifiable, and limiting the level of amplification. Among the strict protocols routinely followed by most laboratories attempting to practice PCR clinically is the use of separate facilities (and often personnel) for those activities that take place prior to PCR (sample preparation and reagent preparation) and for those activities that involve amplification and detection. Although this solution is widely practiced today, it clearly is very inconvenient in most institutions. Chemical and enzymatic methods of treating PCR products to minimize or prevent reamplification include the use of uracil N-glycosylase, the use of PCR primers terminating with ribose at their 3'-ends, and the use of isopsoralens. While somewhat effective, it is not yet obvious that these methods will circumvent the need for separate facilities for preamplification activities and for amplification and detection.

In organism or native template false positive results, the false positive often cannot be distinguished from an actual positive because the false positive and an actual positive share an identical sequence. In cases where positives are identified by DNA melting, the organism or native template false positive and an actual positive have the same melting point. Because an organism or native template false positive and an actual positive have the same sequence and the same physical characteristics, the origin of the false positive cannot be distinguished or ascertained. Moreover, if the lab in question is testing for rare or dangerous pathogens (e.g., Ebola virus), a false positive may be quite alarming and may falsely trigger a response (e.g., quarantine) as though a subject is infected with a real, dangerous pathogen. Clinical laboratories have traditionally used organism or well-characterized clinical positive samples that contain the organism for validation and quality control of diagnostic tests. This can be a problem if the organisms being tested are difficult to propagate (e.g. *Coxiella burnetii*) or highly pathogenic (e.g., Ebola virus) in that they may be difficult to obtain, or, if they can be obtained, they may require biosafety level 3 or 4 containment. This is not practical for most users.

In addition, because ECMs are designed to determine if an assay is working and that it will correctly identify a true positive clinical specimen, it is generally regarded that ECMs should be at a concentration close to the limit of detection (LOD) of an assay, e.g., 1-100×, 5-50×, or, preferably, about 2-10× of LOD. Using well-characterized positives, inactivated organism, or synthetic nucleic acid template as ECMs often requires some degree of sample preparation and/or aliquoting of the standard(s) in order to ensure that each standard in the ECM is close to the LOD for the assay. This generally means that highly skilled and trained operators are needed in a lab to prepare ECMs and such personnel are not always available in all laboratories—e.g., at CLIA-waived test sites. Preparation and aliquoting of standards is also a potential avenue for contamination of the standards and the lab space. If the lab is validating for dangerous organisms (e.g., Ebola virus), then the live organism ECMs may need to be prepared in a level 3 or 4 containment facility. Again, this is not practical for most clinical laboratories.

In addition, well-characterized positives, inactivated organism, and synthetic nucleic acid template may require special storage and handling (e.g., storage at −80° C.). This makes manufacture, shipping, and storage more costly, and may limit assay validation and use to laboratories with appropriate cold-chain storage. This is not practical in all clinical laboratories, particularly CLIA-waived physician-offices. Use of ECMs with room temperature or elevated temperature stability limits is less expensive and more broadly applicable.

Accordingly, there are a number of disadvantages with existing external control material systems and methods.

BRIEF SUMMARY

Solutions to the Problems

Embodiments of the present disclosure solve one or more of the foregoing or other problems in the art with novel external control material. The external control material described herein includes a set of positive control sequences that are engineered to minimize the likelihood of detecting a false positive result. Each positive control sequence is designed to be amplified with the same forward and reverse primers as the test sequences in an assay that corresponds to each positive control sequence, but each positive control sequence in the ECM includes an engineered sequence that is distinguishable from the corresponding test amplicons to allow users to distinguish between ECM and test positives. For example, the amplified positive control sequences in the ECM may be melt-shifted relative to the corresponding test sequence amplicons. An engineered sequence (i.e., an ECM-specific sequence) may be a synthetic sequence or a natural sequence, so long as it is different and detectably distinguishable from the original pathogen sequence. In addition, in some illustrative embodiments the positive control sequences in the ECM are designed to be run in a multiplex environment (e.g., a high-order multiplex). In a preferred embodiment, the ECMs described herein contain no biological hazards and are non-infectious. Likewise, they do not require any special handling or sample preparation or aliquoting and are room-temperature stable.

Described herein are:

1. A positive control material comprising,
 a sample collection delivery device having dried therein a plurality of positive control sequences configured to be resuspended when a fluid is added,
 wherein each of the positive control sequences comprises an engineered sequence configured to minimize obtaining a false positive result, and wherein the sample collection delivery device does not contain a test sample or one or more test sequences, and
 wherein the engineered sequence of each positive control sequence is selected to have a melting temperature different and/or distinguishable from a melting temperature of a corresponding test sequence.

2. The positive control material of clause 1 wherein each positive control sequence melts in a melt window at a temperature in a range of about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melt window of the corresponding test sequence.

3. The positive control material of at least one of clause 1 or clause 2, wherein there are from about 2 to about 10 positive control sequences dried in the sample collection delivery device.

4. The positive control material of one or more of clauses 1 to 3, wherein there are from about 2 to about 20 positive control sequences dried on or in the sample collection delivery device.

5. The positive control material of one or more of clauses 1 to 4, wherein there are from about 2 to about 30 positive control sequences dried on or in the sample collection delivery device.

6. The positive control material of one or more of clauses 1 to 5, wherein there are from about 2 to about 40 positive control sequences dried on or in the sample collection delivery device.

7. The positive control material of one or more of clauses 1 to 6, wherein the sample collection delivery device is provided for easy transfer of the positive control sequences to an assay device.

8. The positive control material of one or more of clauses 1 to 7, wherein the sample collection delivery device is a swab.

9. The positive control material of one or more of clauses 1 to 8, wherein the sample collection delivery device is a vial that comprises a vial body having an interior volume for receiving a fluid and a cannula extending away from an exterior of a bottom surface of the vial body, the cannula being configured to deliver a sample to be analyzed to a multiplex assay device.

10. The positive control material of one or more of clauses 1 to 9, wherein each positive control sequence is engineered to melt at a higher temperature or a lower temperature than each corresponding test sequence.

11. A method of controlling a multiplexed PCR system using a positive control material comprising the steps of:
 providing an assay device comprising a first reaction chamber provided with a plurality of primers for multiplexed nucleic acid amplification, amplifying a plurality of positive control sequences in the first reaction chamber to yield a plurality of positive control amplicons, wherein the positive control material does not contain a test sample, and detecting the positive control amplicons, wherein detecting each of the positive control amplicons indicates that the multiplexed PCR system is operating correctly, and wherein each amplified positive control sequence melts at a different and/or distinguishable temperature from its corresponding test sequence as a result of the presence of the engineered sequences in the positive control sequences.

12. The method of clause 11, wherein each positive control sequence melts in a melt window at a temperature in a range of about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melt window of the corresponding test sequence.

13. The method of clause 11 and/or clause 12, wherein each positive control sequence and its corresponding test sequence comprise the same forward and reverse primer binding sites for the plurality of primers and wherein the engineered sequences are between forward and reverse primer binding sites.

14. The method of one or more of clause 11 to clause 13, wherein the amplifying step includes amplifying from about 2 to about 10 unique positive control sequences in the assay device.

15. The method of one or more of clause 11 to clause 14, wherein the amplifying step includes amplifying from about 2 to about 20 unique positive control sequences in the assay device.

16. The method of one or more of clause 11 to clause 15, wherein the amplifying step includes amplifying from about 2 to about 30 unique positive control sequences in the assay device.

17. The method of one or more of clause 11 to clause 16, wherein the amplifying step includes amplifying from about 2 to about 40 unique positive control sequences in the assay device.

18. The method of one or more of clause 11 to clause 17, the assay device further comprising at least a second reaction chamber fluidly connected to the first reaction chamber, the second reaction chamber comprising primer pairs configured for further amplification of each of the positive control sequences, and wherein the method further comprises further amplifying the positive control sequences, wherein the further amplifying step occurs prior to the detecting step.

19. The method of one or more of clause 11 to clause 18, wherein the second-stage reaction chamber includes an array of wells with each well having at least one primer pair therein for further amplification of each of the positive control sequences.

20. The method of one or more of clause 11 to clause 19, wherein detecting the positive control amplicons includes observing a DNA melting signal for each of the positive control amplicons, wherein the DNA melting signal is at the different and/or distinguishable temperature as compared to the melting temperatures of the test sequences that correspond to each positive control amplicon.

21. The method of one or more of clause 11 to clause 20, further comprising providing a second assay device comprising a first reaction chamber provided with a plurality of primers for multiplexed nucleic acid amplification, amplifying a negative sample in the first reaction chamber, wherein the positive control material does not contain a test sample, and detecting a negative result for each of the positive control amplicons, and wherein detecting the negative result for each of the positive control amplicons indicates that the multiplexed PCR system is operating correctly.

22. The method of one or more of clause 11 to clause 21, further comprising including at least one test sequence with the plurality of positive control sequences in the assay device.

23. The method of one or more of clause 11 to clause 22, wherein the positive control sequences can be used to determine the concentration of at least one test sequence.

24. An assay device for a multiplexed nucleic acid amplification system comprising, a plurality of positive control sequences, and a first reaction chamber in the assay device provided with a plurality of primers for multiplex amplification of the positive control sequences and corresponding test sequences, wherein each positive control sequence comprises an engineered sequence configured to minimize obtaining a false positive result from the positive control sequences, wherein each positive control sequence binds a different primer sequence of the plurality of primers within the first reaction chamber, and wherein the first reaction chamber does not contain a test sample or test sequences.

25. The assay device of clause 24, wherein non-specific binding of the primers to the engineered sequence is minimized.

26. The assay device of clause 24 and/or clause 25, wherein each positive control sequence has a melting temperature different and/or distinguishable from its corresponding test sequence.

27. The assay device of one or more of clause 24 to clause 26, wherein there are from about 2 to about 10 positive control sequences.

28. The assay device of one or more of clause 24 to clause 27, wherein there are from about 2 to about 20 positive control sequences.

29. The assay device of one or more of clause 24 to clause 28, wherein there are from about 2 to about 30 positive control sequences.

30. The assay device of one or more of clause 24 to clause 29, wherein there are from about 2 to about 40 positive control sequences.

31. The assay device of one or more of clause 24 to clause 30, further comprising at least a second reaction chamber in the assay device fluidly connected to the first reaction chamber, the second reaction chamber comprising primer pairs configured for further amplification of each of the positive control sequences and the corresponding test sequences.

32. A method of detecting a plurality of primer pairs configured to amplify a plurality of test sequences within a multiplexed nucleic acid amplification system, comprising the steps of:

providing a positive control material comprising a plurality of positive control sequences, each positive control sequence comprising an engineered sequence configured to minimize observing a false positive result relative to a corresponding test sequence, wherein each amplified positive control sequence melts at a temperature different and/or distinguishable from its corresponding test sequence as a result of the presence of the engineered sequence, providing an assay device that includes a reaction container comprising the plurality of primers for amplification of each of the positive control sequences, amplifying the plurality of positive control sequences in the reaction container, wherein the positive control material does not contain a test sample or a test sequence, and detecting a melt signal for each amplified positive control sequence in the reaction container, wherein a melt signal of each of the plurality of positive control sequences indicates presence of each corresponding primer pair in the reaction container.

33. The method of clause 32, wherein each positive control sequence and its corresponding test sequence comprise the same forward and reverse primer binding sites for one of the plurality of primer pairs and wherein the engineered sequences are between forward and reverse primer binding sites.

34. The method of clause 32 and/or clause 33, wherein the amplifying step includes simultaneously amplifying from about 2 to about 10 unique positive control sequences in the reaction container.

35. The method of one or more of clause 32 to clause 34, wherein the amplifying step includes simultaneously amplifying from about 2 to about 20 unique positive control sequences in the reaction container.

36. The method of one or more of clause 32 to clause 35, wherein the amplifying step includes simultaneously amplifying from about 2 to about 30 unique positive control sequences in the reaction container.

37. The method of one or more of clause 32 to clause 36, wherein the amplifying step includes simultaneously amplifying from about 2 to about 40 unique positive control sequences in the reaction container.

38. The method of one or more of clause 32 to clause 37, wherein the positive control material is provided in a vessel configured for loading into the reaction container.

39 The method of one or more of clause 32 to clause 38, wherein the detecting step includes using a melt window for each positive control sequence that is different from a melt window for each corresponding test sequence.

40. The method of one or more of clause 32 to clause 39, wherein the melt window for each positive control sequence is about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than the melt window of the corresponding test sequence.

41. The method of one or more of clause 32 to clause 40, further comprising providing a negative control sample, providing a second reaction container comprising the plurality of primers for amplification of each of the positive control sequences, exposing the negative control sample to amplification conditions in the second reaction container, and determining whether any melt signals are present, wherein presence of a melt signal indicates contamination.

42. The method of one or more of clause 32 to clause 41, wherein the presence of the melt signal in the melt window for one of the positive control sequences indicates contamination by the positive control sequence or its amplicon, and the presence of the melt signal in the melt window for one of the corresponding test sequences indicates contamination by a test sequence or its amplicon.

43. An external control kit comprising, a sample collection vial having dried therein a plurality of positive control sequences configured to be resuspended when a fluid is added to the sample collection vial, wherein each positive control sequence has a shifted melting temperature relative to and distinguishable from a corresponding test sequence, and a software module for programming an instrument to amplify the plurality of positive control sequences in a multiplexed assay system and to detect the positive control sequences as distinct from the corresponding test sequences.

44. The kit of clause 43, wherein each positive control sequence is engineered to melt at a higher temperature or a lower temperature than each corresponding test sequence.

45. The kit of clause 43 and/or clause 44, wherein each positive control sequence melts in a melt window at a temperature in a range of about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melting point window of the corresponding test sequence.

46. The kit of one or more of clause 43 to clause 45, wherein there are from about 2 to about 10 positive control sequences dried in the sample collection vial.

47. The kit of one or more of clause 43 to clause 46, wherein there are from about 2 to about 20 positive control sequences dried in the sample collection vial.

48. The kit of one or more of clause 43 to clause 47, wherein there are from about 2 to about 30 positive control sequences dried in the sample collection vial.

49. The kit of one or more of clause 43 to clause 48, wherein there are from about 2 to about 40 positive control sequences dried in the sample collection vial.

50. The kit of one or more of clause 43 to clause 49, wherein the sample collection vial comprises a vial body having an interior volume for receiving a fluid and a cannula extending away from an exterior of a bottom surface of the vial body, the cannula being configured to deliver a sample to be analyzed to the multiplexed assay.

51. The kit of one or more of clause 43 to clause 50, wherein the software module defines a melt window for each amplicon derived from each of the positive control sequences that is different from and distinguishable from a positive amplicon melt window for each amplicon derived from test sequences corresponding to each of the positive control sequences.

52. The kit of one or more of clause 43 to clause 51, wherein the software module is configured to interrogate the melt transition window for each amplicon derived from each of the positive control sequences and the positive amplicon window for each amplicon derived from the test sequences, and wherein the software module is further configured to distinguish between positive control contamination and organism or test sequence contamination.

53. A system for multiplexed nucleic acid amplification comprising, a plurality of positive control sequences, an assay device comprising a first reaction chamber provided with a plurality of primers for multiplexed nucleic acid amplification, an instrument configured to receive the assay device and to perform a nucleic acid amplification reaction to produce a plurality of positive control amplicons and to detect the positive control amplicons, and a software module for instructing the instrument to amplify the plurality of positive control sequences and to detect the positive control amplicons, wherein the positive control sequences amplicons have at least one detectable sequence property that is different and/or distinct from a corresponding plurality of test sequences, wherein each positive control sequence comprises an engineered sequence configured to minimize a false positive resulting from the positive control sequences, and wherein each positive control sequence binds a different primer sequence of the plurality of primers within the assay device.

54. The system of clause 53, wherein each positive control sequence is engineered to melt at a higher temperature or a lower temperature as compared to each corresponding test sequence.

55. The system of clause 53 and/or clause 54, wherein each positive control sequence melts in a melt window at a temperature in a range of about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melt window of the corresponding test sequence.

56. The system of one or more of clause 53 to clause 55, wherein the system includes from about 2 to about 10 positive control sequences.

57. The system of one or more of clause 53 to clause 56, wherein the system includes from about 2 to about 20 positive control sequences.

58. The system of one or more of clause 53 to clause 57, wherein the system includes from about 2 to about 30 positive control sequences.

59. The system of one or more of clause 53 to clause 58, wherein the system includes from about 2 to about 40 positive control sequences.

60. The system of one or more of clause 53 to clause 59, further comprising a sample collection vial having the positive control sequences dried therein.

61. The system of one or more of clause 53 to clause 60, wherein the software module defines a melt window for each amplicon derived from each of the positive control sequences that is different from and distinguishable from a positive amplicon melt window for each amplicon derived from test sequences corresponding to each of the positive control sequences.

62. The system of one or more of clause 53 to clause 61, wherein the software module is configured to interrogate the melt transition window for each amplicon derived from each of the positive control sequences and the positive amplicon window for each amplicon derived from the test sequences to distinguish between positive control contamination and organism or test sequence contamination.

63. The system of one or more of clause 53 to clause 62, the assay device further comprising at least a second reaction chamber fluidly connected to the first reaction chamber, the second reaction chamber comprising primer pairs configured for further amplification of each of the positive control sequences.

64. The system of one or more of clause 53 to clause 63, wherein the second reaction chamber includes two or more reaction wells configured for further amplification of the positive control sequences, and wherein at least one of the two or more reaction wells includes two or more primer pairs for simultaneous amplification of two or more positive control sequences.

65. The system of one or more of clause 53 to clause 64, wherein the assay device comprises a first-stage reaction chamber provided with a plurality of primers for multiplex amplification of the positive control sequences, and a second-stage reaction chamber fluidly connected to the first-stage reaction chamber, wherein the second-stage reaction chamber includes an array of wells with each well having at least one primer pair therein for further amplification each of the positive control sequences.

66. The system of one or more of clause 53 to clause 65, wherein at least one well of the array of wells includes two or more primer pairs for simultaneous amplification of two or more positive control sequences.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description that follows, and in part will be obvious from the description, or may be learned by the practice of the invention. The features and advantages may be realized and obtained by means of the instruments and combinations particularly pointed out in the appended claims. These and other features will become more fully apparent from the following description and appended claims, or may be learned by the practice of the invention as set forth hereinafter.

DETAILED DESCRIPTION

Figure 1:
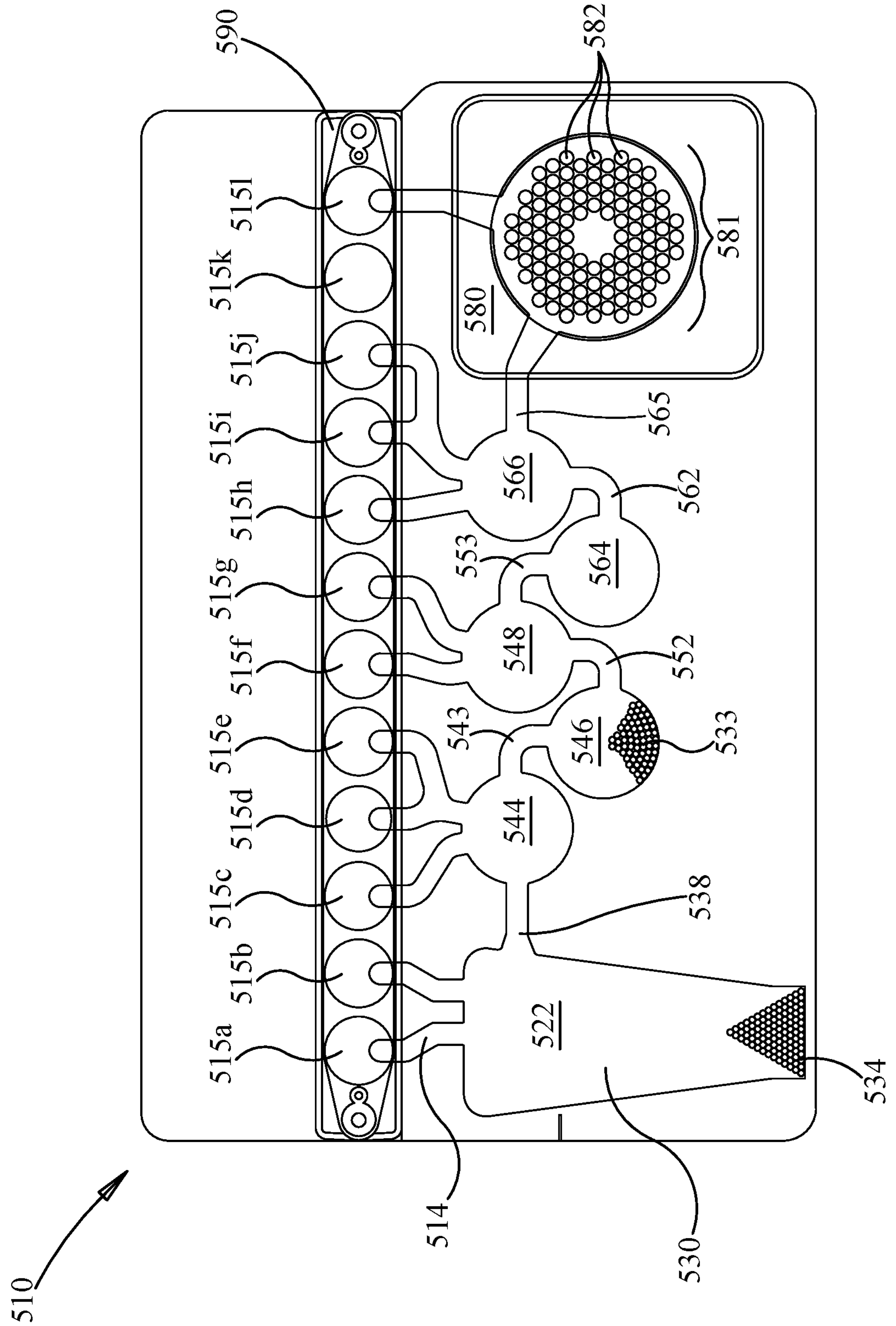
FIG. 1 shows a flexible pouch useful for self-contained PCR.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g., a polypeptide or nucleic acid); or a solution containing a non-naturally occurring nucleic acid, drugs or pharmaceuticals and drug process precursors (e.g., biologics, drugs, injectables, bioreactor components, etc.) which may be assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids. Samples may also include environmental samples such as, but not limited to, soil, water (fresh water, waste water, etc.), air monitoring system samples (e.g., material captured in an air filter medium), surface swabs, and vectors (e.g., mosquitos, ticks, fleas, etc.).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, mRNA, rRNA, cDNA, gDNA, ssDNA, dsDNA, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically to occur at about a melting temperature (Tm) minus 5° C. (i.e. 5° below the Tm of the probe). Functionally, high stringency conditions are used to identify nucleic acid sequences having at least 80% sequence identity.

As used herein, the term 'canonical sequence' (the term 'consensus sequence' is synonymous and also commonly used in the art) refers to the calculated order of most frequent nucleotide residues found at each position in a sequence alignment. The canonical sequence represents the results of multiple sequence alignments in which related sequences are compared to each other and similar sequence motifs are calculated. The panels referred to herein are often designed to detect a set of organisms. For each organism in a panel, the known variants of that organism typically have some sequence differences within the amplicons amplified by the panel. Thus, for most assays, it is generally not accurate to refer to one pathogen sequence because each pathogen in the panel represents a population of closely related sequence variants. Thus, the amplicons for a given organism represent all of the variants within the detected population—i.e., the canonical sequence. While the term 'canonical sequence' may be generally more accurate, the term 'pathogen sequence' is used synonymously herein. While many assays use a canonical sequence, some assays may use a native sequence, particularly where there is little variation between included strains for a particular target sequence. The term 'canonical sequence' is meant to include such sequences as well.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles, doubling time, or crossing point (Cp), and additional reaction time may be added where additional PCR cycles are added in the embodiments described herein. It is understood that protocols may need to be adjusted accordingly.

As used herein, the term "crossing point" (Cp) (or, alternatively, cycle threshold (Ct), quantification cycle (Cq), or a synonymous term used in the art) refers to the number of cycles of PCR required to obtain a fluorescence signal above some threshold value for a given PCR product (e.g., target or internal standard(s)), as determined experimentally. The cycle where each reaction rises above the threshold is dependent on the amount of target (i.e., reaction template) present at the beginning of the PCR reaction. The threshold value may typically be set at the point where the product's fluorescence signal is detectable above background fluorescence; however, other threshold values may be employed. As an alternative to setting a somewhat arbitrary threshold value, Cp may be determined by calculating the point for a reaction at which a first, second, or nth order derivative has its maximum value, which determines the cycle at which the curvature of the amplification curve is maximal. An illustrative derivative method was taught in U.S. Pat. No. 6,303,305, herein incorporated by reference in its entirety. Nevertheless, it usually does not matter much where or how the threshold is set, so long as the same threshold is used for all reactions that are being compared. Other points may be used as well, as are known in the art, and any such point may be substituted for Cp, Ct, or Cq in any of the methods discussed herein.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches, methods and devices for loading such pouches, and instruments for use with the pouches, are disclosed in more detail in U.S. Pat. Nos. 8,394,608; and 8,895,295; and U.S. Pat. Pub. No. 2014/0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art.

While the terms "sample well", "amplification well", "amplification container", "reaction chamber", "reaction zone", or the like are used herein, these terms are meant to encompass wells, tubes, and various other reaction containers, as are used in these amplification systems. In one embodiment, a pouch may be an assay device that includes one or more reaction containers or reaction zones. In one embodiment, a pouch may be a flexible container. For instance, a pouch/flexible container may include one or more sample wells, amplification wells, amplification containers, reaction chambers, reaction zones, or the like formed between two or more flexible layers of material. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels **515*a* through 515*l*, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510** is suitable for use in the FilmArray® instrument (BioFire Diagnostics, LLC, Salt Lake City, UT). However, it is understood that the pouch embodiment is illustrative only.

While other containers may be used, illustratively, pouch 510 may be formed of two layers of a flexible plastic film or other flexible material such as polyester, polyethylene terephthalate (PET), polycarbonate, polypropylene, polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington DE) of about 0.0048 inch (0.1219 mm) thick and polypropylene films of 0.001-0.003 inch (0.025-0.076 mm) thick perform well. Illustratively, pouch 510 may be made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of the pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material. Thus, it is understood that when the terms "flexible pouch" or "flexible sample container" or the like are used, only portions of the pouch or sample container need be flexible.

Illustratively, a plastic film may be used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton WI), illustratively regulated at an operating temperature of 195° C., the pneumatic press works like a printing press, melting the sealing surfaces of plastic film only where the die contacts the film. Likewise, the plastic film(s) used for pouch 510 may be cut and welded together using a laser cutting and welding device. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction may be hydrated by an aqueous sample. If the aqueous sample has been heated prior to hydration, this creates the conditions for a true hot-start PCR and reduces or eliminates the need for expensive chemical hot-start components. In another embodiment, components may be provided in powder or pill form and are placed into blisters prior to final sealing.

Pouch 510 may be used in a manner similar to that described in U.S. Pat. No. 8,895,295. In one illustrative embodiment, a 300 μl mixture comprising the sample to be tested (100 μl) and lysis buffer (200 μl) may be injected into an injection port (not shown) in fitment 590 near entry channel **515*a*, and the sample mixture may be drawn into entry channel 515*a*. Water may also be injected into a second injection port (not shown) of the fitment 590 adjacent entry channel 515*l*, and is distributed via a channel (not shown) provided in fitment 590, thereby hydrating up to eleven different reagents, each of which were previously provided in dry form at entry channels 515*b* through 515*l*. Illustrative methods and devices for injecting sample and hydration fluid (e.g. water or buffer) are disclosed in U.S. Pat. Pub. No. 2014/0283945, which was already incorporated by reference in its entirety herein above, although it is understood that these methods and devices are illustrative only and other ways of introducing sample and hydration fluid into pouch 510 are within the scope of this disclosure. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590**, see U.S. Pat. No. 8,895,295, already incorporated by reference.

After injection, the sample may be moved from injection channel **515*a* to lysis blister 522 via channel 514. Lysis blister 522 is provided with beads or particles 534, such as ceramic beads or other abrasive elements, and is configured for vortexing via impaction using rotating blades or paddles provided within the FilmArray® instrument. Bead-milling, by shaking, vortexing, sonicating, and similar treatment of the sample in the presence of lysing particles such as zirconium silicate (ZS) beads 534**, is an effective method to form a lysate. It is understood that, as used herein, terms such as "lyse," "lysing," and "lysate" are not limited to rupturing cells, but that such terms include disruption of non-cellular particles, such as viruses.

Figure 2:
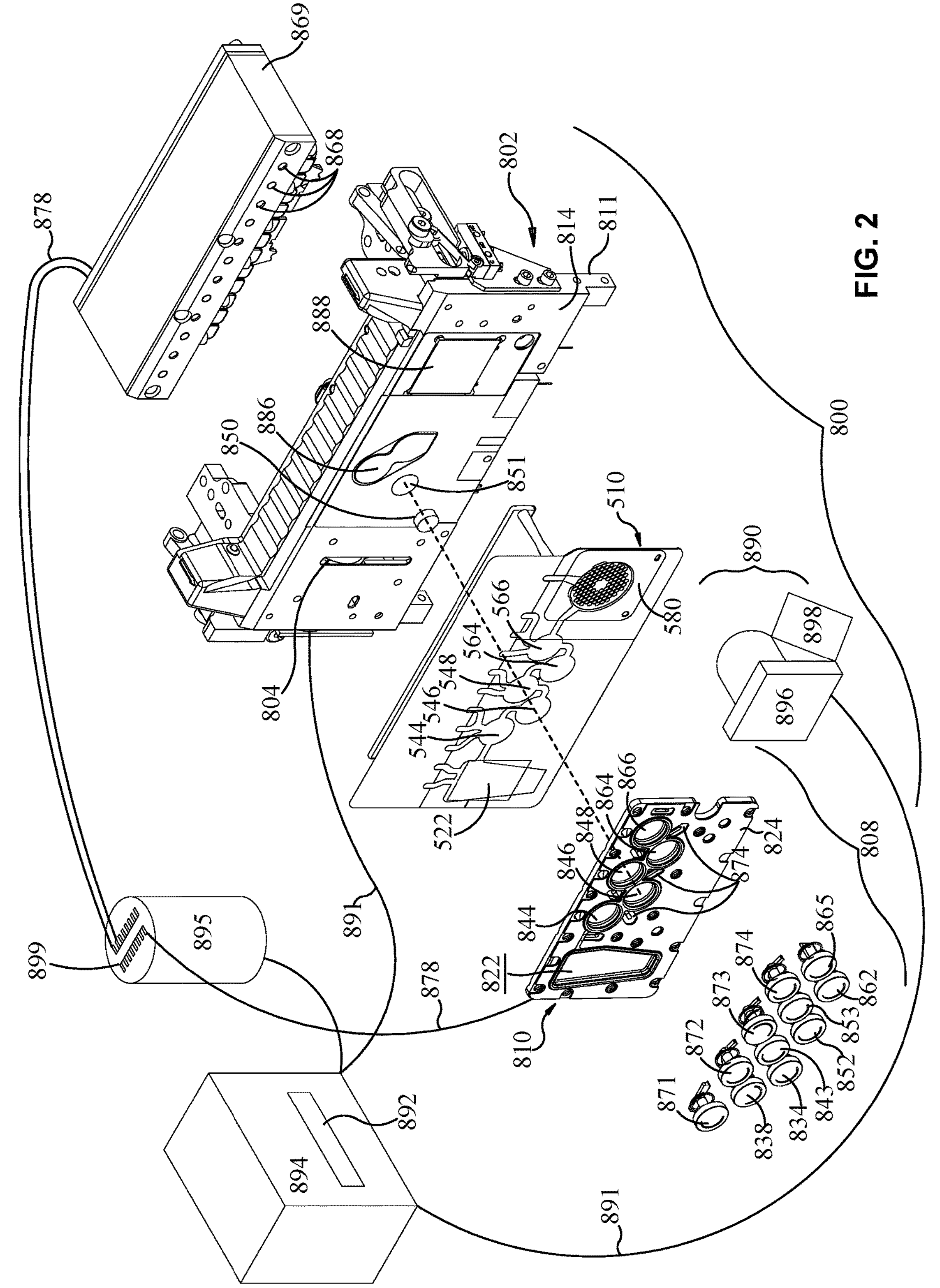
FIG. 2 is an exploded perspective view of an instrument for use with the pouch of FIG. 1, including the pouch of FIG. 1.
Figure 4:
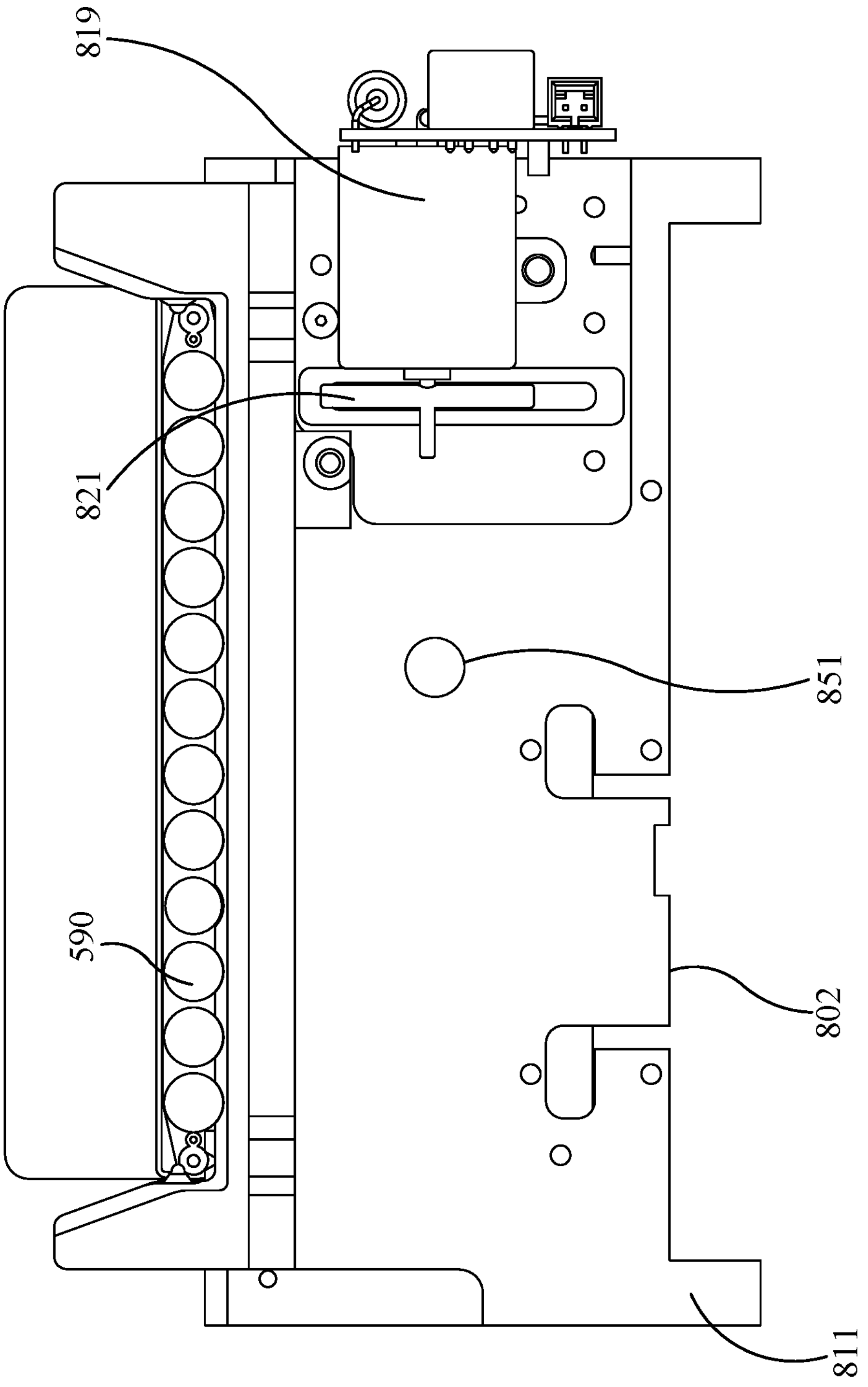
FIG. 4 shows a motor used in one illustrative embodiment of the instrument of FIG. 2.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample. In some embodiments, chemicals or heat may be used in addition to or instead of mechanical lysis.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be rehydrated, illustratively using fluid provided from one of the entry channel 515*c*-515*e*, and then moved through channel 543 to blister 544, and then through channel 538 to blister 522. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more of injection channels 515*c* to 515*e* are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515*f* is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515*g* is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, an RT step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515*i*. Alternatively, a dilution buffer from 515*i* may be moved to blister 566 then mixed with the amplified sample in blister 564 by moving the fluids back and forth between blisters 564 and 566. If desired, dilution may be repeated several times, using dilution buffer from injection channels 515*j* and 515*k*, or injection channel 515*k* may be reserved, illustratively, for sequencing or for other post-PCR analysis, and then adding second-stage PCR master mix from injection channel 515*h* to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously or individually thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
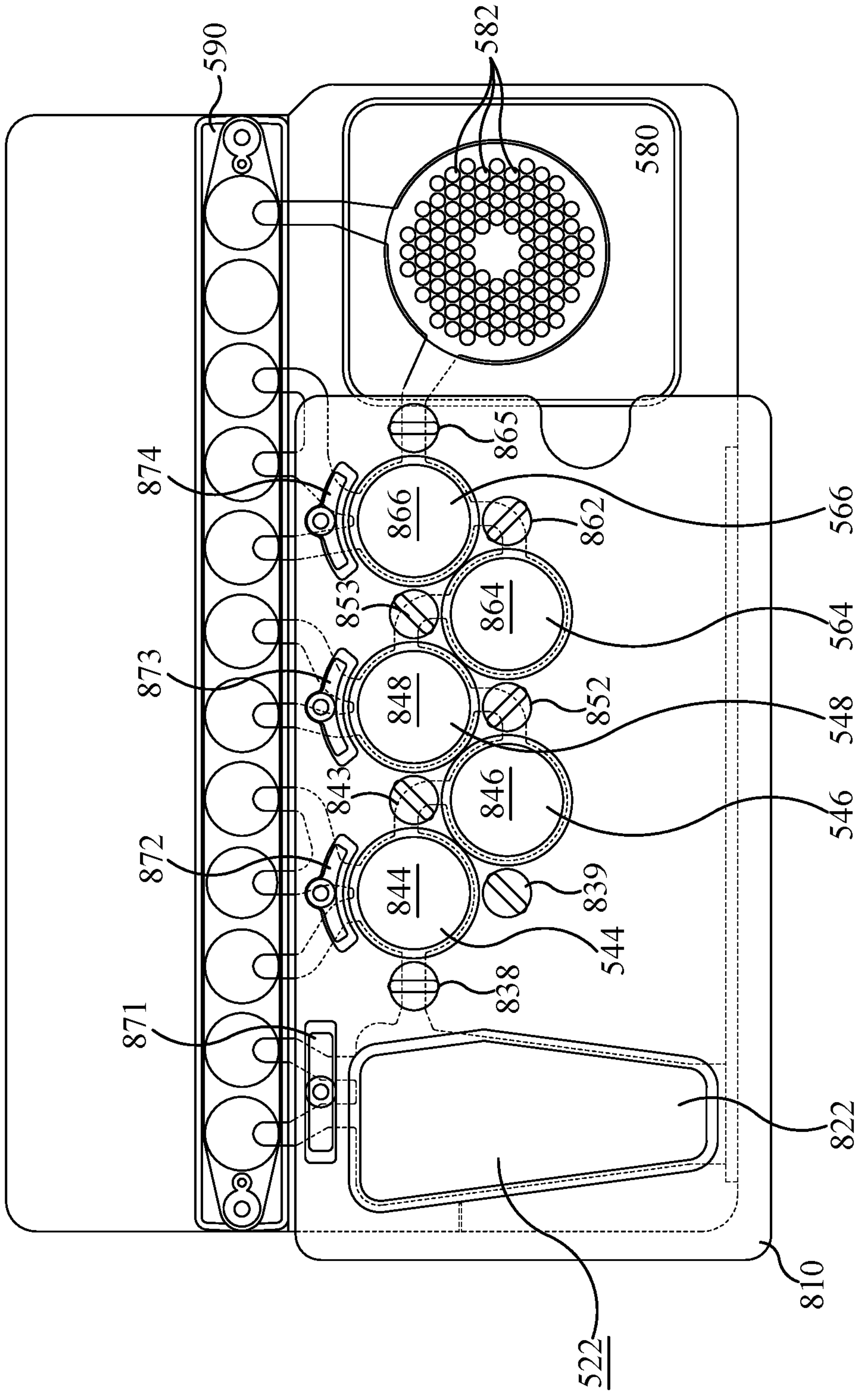
FIG. 3 shows a partial cross-sectional view of the instrument of FIG. 2, including the bladder components of FIG. 2, with the pouch of FIG. 1.

When pneumatic pressure is used to move materials within pouch 510, in one embodiment, a “bladder” may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention. Alternatively, an array or mechanical actuators and seals may be used to seal channels and direct movement of fluids between blisters. A system of mechanical seals and actuators that may be adapted for the instruments described herein is described in detail in WO 2018/022971, the entirety of which is incorporated herein by reference.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of Taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, 862, and 865 that correspond to channels 538, 543, 552, 553, 562, and 565 of pouch 510, as well as seals 871, 872, 873, 874 that minimize backflow into fitment 590. When activated, hard seals 838, 843, 852, 853, 862, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned such that a small number of actuators could be used for several of the processing stations including sample disruption, nucleic-acid capture, first and second-stage PCR, and processing stations for other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term “pneumatic actuator” is used herein, it is understood that other actuators and other ways of providing pressure may be used, depending on the configuration of the pouch and the instrument.

Turning back to FIG. 2, each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention. Similar pneumatic control may be provided in the embodiments of FIGS. 1-4, for control of fluids in pouch 510, or other actuators, servos, or the like may be provided.

Several other components of instrument 800 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is fully retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required. It is understood that similar magnets and methods for activating the magnets may be used in the embodiments of FIGS. 12-16.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of temperature control elements are mounted on a second side 814 of support 802. As used herein, the term “temperature control element” refers to a device that adds heat to or removes heat from a sample. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

As discussed above, first-stage heater 886 may be positioned to heat and cool the contents of blister 564 for first-stage PCR. As seen in FIG. 2, second-stage heater 888 may be positioned to heat and cool the contents of second-stage blisters 582 of array 581 of pouch 510, for second-stage PCR. It is understood, however, that these heaters could also be used for other heating purposes, and that other heaters may be included, as appropriate for the particular application.

As discussed above, while Peltier devices, which thermocycle between two or more temperatures, are effective for PCR, it may be desirable in some embodiments to maintain heaters at a constant temperature. Illustratively, this can be used to reduce run time, by eliminating time needed to transition the heater temperature beyond the time needed to transition the sample temperature. Also, such an arrangement can improve the electrical efficiency of the system as it is only necessary to thermally cycle the smaller sample and sample vessel, not the much larger (more thermal mass) Peltier devices. For instance, an instrument may include multiple heaters (i.e., two or more) at temperatures set for, for example, annealing, elongation, denaturation that are positioned relative to the pouch to accomplish thermal cycling. Two heaters may be sufficient for many applications. In various embodiments, the heaters can be moved, the pouch can be moved, or fluids can be moved relative to the heaters to accomplish thermal cycling. Illustratively, the heaters may be arranged linearly, in a circular arrangement, or the like. Types of suitable heaters have been discussed above, with reference to first-stage PCR.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible. For example, in some embodiments the second-stage heaters may be on the opposite side of pouch 510 from that shown in FIG. 2. Such orientation is exemplary only and may be determined by spatial constraints within the instrument. Provided that second-stage reaction zone 580 is provided in an optically transparent material, photodetectors and heaters may be on either side of array 581.

As shown, a computer 894 controls valves 899 of compressed air source 895, and thus controls all of the pneumatics of instrument 800. In addition, many of the pneumatic systems in the instrument may be replaced with mechanical actuators, pressure applying means, and the like in other embodiments. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Other prior art instruments teach PCR within a sealed flexible container. See, e.g., U.S. Pat. Nos. 6,645,758, 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. Still, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Illustrative heaters include Peltiers and other block heaters, resistance heaters, electromagnetic heaters, and thin film heaters, as are known in the art, to thermocycle the contents of blister 864 and second-stage reaction zone 580. Bladder plate 810, with bladders 822, 844, 846, 848, 864, 866, hard seals 838, 843, 852, 853, and seals 871, 872, 873, 874 form bladder assembly 808, which may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Quality control ('QC') materials are necessary to ensure proper performance of systems such as the pouch 510 illustrated in FIG. 1 and the instrument 800 illustrated in FIG. 2. Each lot of pouches, like pouch 510, generally needs to be QC tested with positive and negative QC mixes at the time of manufacture to confirm that the pouches were manufactured according to specification, that they are free of contamination, and to confirm that the assays and instruments are operating correctly. Individual batches and entire pouch lots can pass or fail QC based on their performance.

Clinical labs and other laboratories also run QC tests with external control material ('ECM'). Labs run ECMs for slightly different reasons than the reasons for running QC material at the time of manufacture. Clinical laboratories are generally required by accrediting agencies like CLIA to validate new tests prior to offering them for clinical use. Likewise, ECM is run to verify that the performance of the assays matches manufacturer claims, to verify the performance of new lots of assays, to verify assay performance in the hands of new users or when new/repaired instruments are introduced, and to detect system failures and/or highlight problems in the handling and testing of samples. While reference is made herein to clinical labs, it is understood that clinical labs are one illustrative example of users of the subject matter of this disclosure, and that laboratories in many fields run control materials such as ECMs. It is understood that this disclosure is not meant to be limited to clinical labs.

ECM is generally one or a set of matched assay positives and negatives that may be run at or near the same time to verify that the performance of the assays matches manufacturer claims or to verify that the assays in the lot are free of contamination. Typically, ECMs have been well-characterized clinical samples that are known to be positive for one or more pathogens that the assay is designed to detect, live or inactivated organism spiked into a known negative clinical specimen or synthetic nucleic acid template.

Nevertheless, organism and synthetically-produced nucleic acid positive controls have the potential to contaminate future assays and produce false positives. For instance, after amplification a PCR reaction mix may contain as many as $10^{11}$ to $10^{12}$ copies of the original target amplicon. Likewise, clinical specimens and organism stocks may contain $10^{11}$ to $10^{12}$ or more template copies/ml. Risk of contamination from manipulation of these sources is almost as bad or as bad as escaping amplicon. Given the desirability that PCR-based assays for infectious pathogens be sensitive to <50 copies of the target sequence, this means that ~$10^{-8}$ μL (roughly, a billionth of a drop) of the post-amplification mix contains sufficient target to contaminate a subsequent amplification process and cause a false-positive result. Avoiding such carryover contamination, or rendering it harmless, is a difficult challenge.

Disclosed herein is an ECM ('positive control material' is a type of ECM) that includes a set of positive control sequences and matched assay negatives. The positive control sequences are engineered to minimize the likelihood of detecting a false positive result as a consequence of contamination of subsequent assays with ECM. In addition, the positive control sequences disclosed herein allow users to distinguish between assay contamination with an organism, a test sample that includes a test organism, a test sequence derived from a test organism, or a native amplicon and contamination by the positive control sequences themselves. Each positive control nucleic acid (e.g., DNA or RNA) segment described herein contains sequences that are recognized and amplified by the primers specific for one assay. For instance, the FilmArray® Respiratory Panel (RP) EZ tests for a set of 14 respiratory viral and bacterial pathogens. RP EZ is a CLIA-waived version of the Respiratory Panel (RP). A CLIA-waived test like RP EZ may be a good candidate for the ECM described herein because CLIA-waived tests are designed to be run by people who do not necessarily have technical training and are, thus, not necessarily qualified for preparation or manipulation of live organism standards. Likewise, sites for CLIA-waived tests are not necessarily equipped for safe or appropriate cold-chain storage of live organism standard. However, it is understood that CLIA-waived tests are just one exemplary type of test for which the present disclosure may be appropriate. Products according to the disclosure herein may be appropriate in many settings across multiple industries.

An ECM for the RP EZ Panel might include positive control sequences recognized and amplified by the inner and outer primers specific for each of the 14 different respiratory viral and bacterial pathogens in the RP EZ Panel. ECM sequences may each include approximately 10-50 (e.g., 25) base pairs of canonical pathogen sequence on either side of the outer primer sequence plus the canonical pathogen sequences for the outer and inner forward and reverse primer pairs. However, it is understood that one-step PCR may be used or the primers may be the same in two-step PCR, in which case only one pair of primer sequences may be needed. In contrast to organism and native nucleic acid positive controls, the original canonical pathogen sequence inside the two innermost primer recognition sites of the ECMs described herein is replaced with an ECM-specific sequence that is different than the original canonical pathogen sequence. The ECM-specific sequence may be a synthetic sequence or a natural sequence, so long as it is different and detectably distinguishable from the original canonical pathogen sequence.

Figure 5:
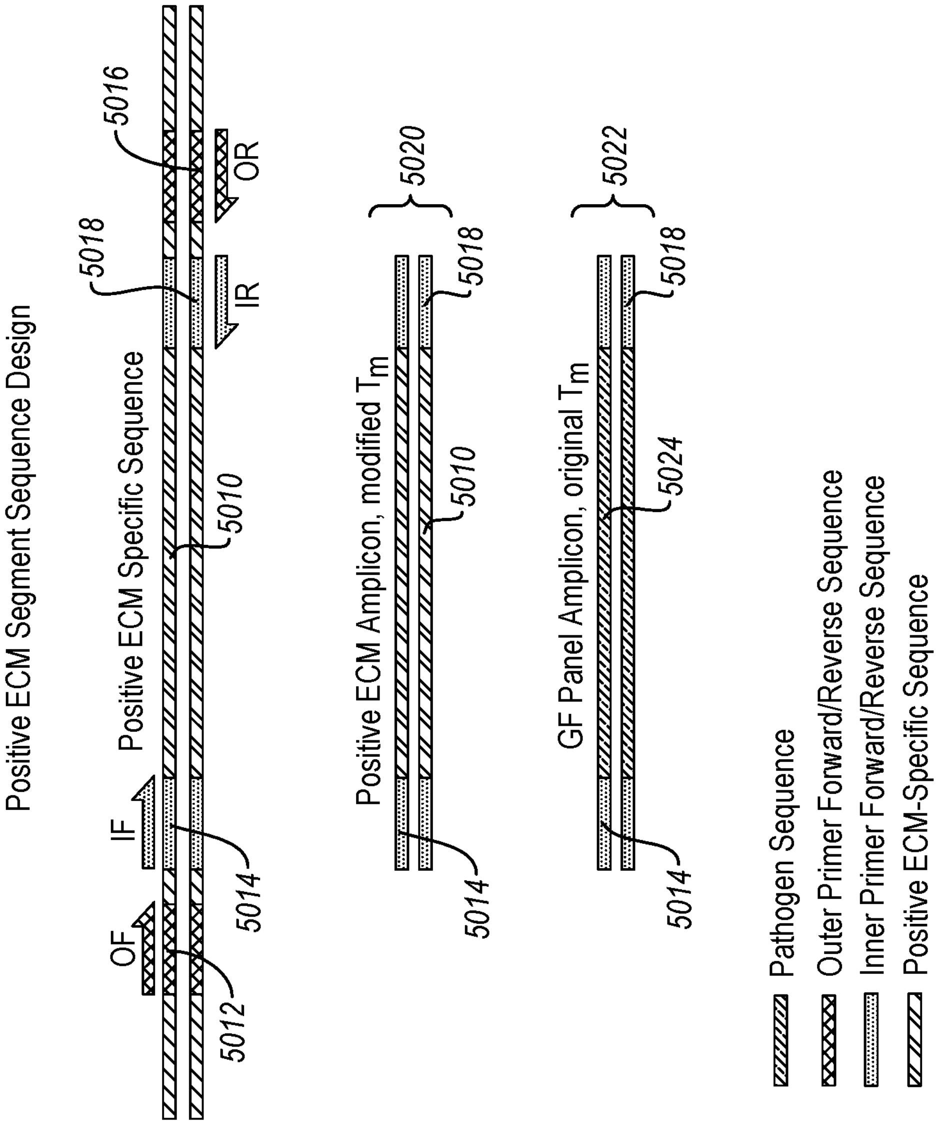
FIG. 5 illustrates positive ECM segment sequence design.

An example of the scheme for designing ECM segments is illustrated in FIG. 5. In one embodiment, when the organism sequence is redesigned to make the ECM, the binding sites for the outer, first-stage PCR primers (5012 and 5016) and inner, second-stage primers (5014 and 5018) are kept substantially unchanged, but the original pathogen sequence 5024 interior to the inner primers 5014 and 5018 is replaced in whole or part with a positive ECM-specific sequence 5010. In the illustrated embodiment, the ECM-specific sequence 5010 replaces the entire pathogen sequence 5024 interior to the inner primers 5014 and 5018 with an engineered, non-native sequence. However, in other embodiments (not shown) the engineered positive ECM-specific sequence 5010 may only replace a portion of the pathogen sequence or may be added to the pathogen sequence. In the illustrated embodiment, the positive ECM amplicon 5020, which comprises the inner primers 5014 and 5018 and the positive ECM-specific sequence 5010, has a modified melting point relative to the test amplicon, which comprises the inner primers 5014 and 5018 and the pathogen sequence 5024.

In one embodiment, the intra-primer region of the ECMs described herein may be replaced with a synthetic sequence that is readily distinguishable from the native sequence by one or more physical means. For example, each native intra-primer sequence of the positive controls may be altered with a synthetic sequence that alters the denaturation characteristics (Tm) of the resulting amplicon. As a consequence, each positive control sequence is amplified by one set of the primer pairs in the panel (some panel analytes may be interrogated by multiple assays, requiring multiple ECM segments to fully test for the presence of all primers associated with that analyte), but the resulting ECM amplicon is melt-shifted and preferably not detected within the target temperature melt window for the pathogen amplicon.

Figure 7:
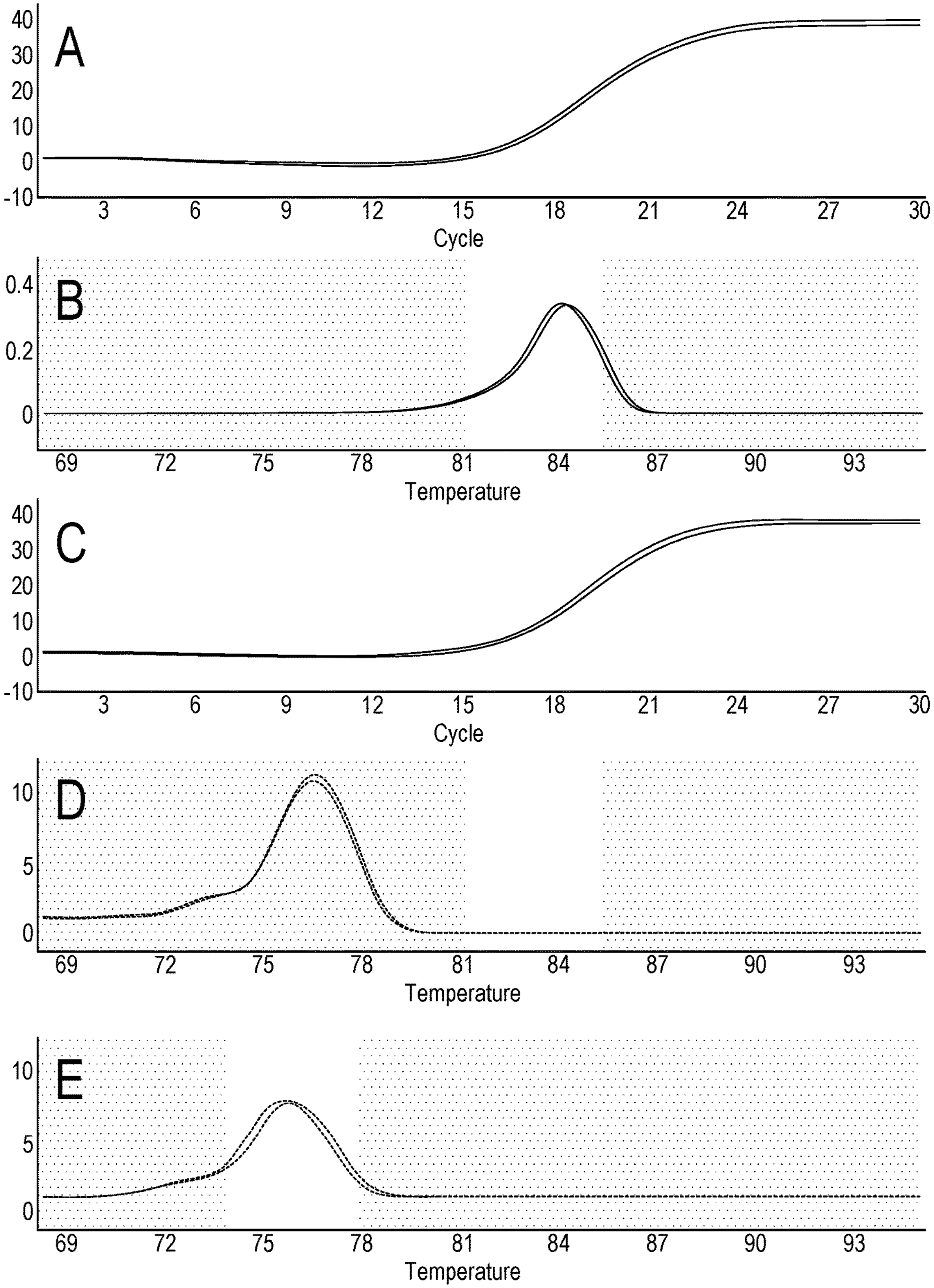
FIGS. 7A and 7B illustrate amplification (FIG. 7A) and amplicon melting (FIG. 7B) of Crimean-Congo hemorrhagic fever (CCHF) virus within the target window (FIG. 7B).
FIGS. 7C and 7D illustrate amplification (FIG. 7C) and amplicon melting (FIG. 7D) of CCHF1 External Control Material (ECM) outside the target window (FIG. 7D).
FIG. 7E illustrates amplicon melting of a CCHF1 External Control Material (ECM) inside the ECM-specific melt window.

As is illustrated, for example, in FIGS. 7B and 7D, the population of amplicons resulting from pathogen sequences melts in an assay-specific window (FIG. 7B) and the ECM-specific amplicon melts at a different temperature outside the window for the corresponding pathogen sequence (FIG. 7D). FIG. 7E illustrates detection of melting of an ECM amplicon in an ECM-specific melt window defined by an ECM-specific instrument software module. In one embodiment, the ECM-specific insert may be designed to raise or lower the melt temperature window of the ECM-specific amplicon by at least +/−2° C. relative to the Tm window of the corresponding pathogen sequence. In another embodiment, the ECM-specific amplicon may melt in a melt window at a temperature in a range of about 2-14° C., 2-13° C., 2-12° C., 2-11° C., 2-10° C., 2-9° C., 2-8° C., 2-7° C., 2-6° C., 2-5° C., 2-4° C., 2-3° C., 3-14° C., 3-13° C., 3-12° C., 3-11° C., 3-10° C., 3-9° C., 3-8° C., 3-7° C., 3-6° C., 3-5° C., 3-4° C., 4-14° C., 4-13° C., 4-12° C., 4-11° C., 4-10° C., 4-9° C., 4-8° C., 4-7° C., 4-6° C., 4-5° C. or any combination thereof higher or lower than the Tm window of the corresponding pathogen sequence. In a preferred embodiment, the ECM-specific insert may be designed to raise or lower the melt temperature window of the ECM-specific amplicon by at least +/−2° C., least +/−3° C., or least +/−4° C. relative to the Tm window of the corresponding pathogen sequence. In a typical ECM designed for a panel of assays, the average Tm shift may be about +/−6-9° C., with some Tm shifts being in the range of about +/−2° C. (e.g., ~2.2-2.5° C.) while other shifts may be much greater at about +/−13-14° C. (e.g., ~12.8° C.).

The positive ECM-specific sequences in the positive control materials described herein may be used for validation in multiplex amplification assays where the positive ECM-specific sequences may be exposed to about 1 to 40 (e.g., 30) or more different primer sets. As a result, there may be enormous potential for cross-reaction between the engineered ECM-specific sequences and the primers in the multiplex amplification assay. There also may be enormous potential for cross-reactions between the engineered positive ECM-specific sequences. To minimize cross-reactions such as, but not limited to, self-interactions (e.g., loop formation, dimerization), primer binding to positive ECM-specific insert sequences, and initiation at interior sites, potential sequences for the positive ECM-specific insert sequences were screened extensively. However, the inventors found that if the 2 to 40 (e.g., 30) or more different outer and inner primer sets were screened against long randomized sequences (e.g., about 1000 base pairs) then the alignment systems, based on current computing power, would typically fail. In order to overcome this, shorter sequences (e.g., about 200 bp) were aligned against the outer primers only to identify initial candidates for the engineered ECM-specific sequences with minimal interactions. However, one will appreciate that increases in computing power are likely to allow the outer and inner primers to be aligned against longer sequences. In addition, certain DNA sequence motifs appear to have fewer cross-primer interactions, suggesting they are less common in nature. For example, CCXCCX/TTXTTX or CCCXCCCX/TTTXTTTX. The uneven spacing minimizes unwanted self-interactions. For example, GCGCGCGC can interact in many ways, GGGCGGGC cannot. Once candidates with few primer interactions are found, individual unwanted primer interactions can be eliminated through targeted modifications to the sequence.

In addition, some assays have a relatively high melt temperature and others have relatively low melt temperatures. Thus, multiple ECM-specific sequences may be needed that can move melts up or down in temperature as needed. Final melt temperature is a combination of at least inner primers and the ECM-specific insert sequences. Outer and inner primers are fixed, so multiple ECM-specific insert sequences may need to be evaluated per assay. Thus, multiple ECM-specific insert sequences may be provided for each primer set in order to assess melting shift. In silico melting experiments were performed to calculate the melting transition of the candidate ECM amplicons (i.e., inner primers+the ECM-specific insert) to determine if the candidate was outside the melt window for the corresponding test amplicon. With this approach, unusual melt behavior (e.g., shoulders) can also be avoided.

Once potential cross-reactions were minimized and the melting behavior of the candidate ECM amplicons were characterized in silico, the inventors in this case found that a limited number of ECM-specific insert sequences could be used to engineer ECM amplicons with high and low melt characteristics. For example, for a given panel of assays, 2 or 3 or 4 or 5 or 6 or more (e.g., 3) low-melt standardized ECM inserts and 2 or 3 or 4 or 5 or 6 or more (e.g., 3) high-melt standardized ECM inserts may be assessed. Of course, one will appreciate that the design of ECM insert sequences and ECM amplicons is assay specific because of the differences in primers and test sequences. Thus, for a given panel, more or fewer low-melt standardized ECM inserts and high-melt standardized ECM inserts may be needed.

The applicant is developing these positive controls for a number of reasons. For example, 1) to allow customers and other end users to perform laboratory validations without having to obtain and test rare clinical specimens or analytes that require biosafety level 3 and 4 containment, 2) to reduce the risk of false positive results that could result from contamination of a laboratory with traditional external control materials that includes organisms or materials derived from the same organisms assayed in test samples, 3) the ECMs described herein may be engineered so that they are room-temperature stable, and 4) the ECMs may be pre-made to allow for no user manipulation of high concentration stocks and clinical specimens (reducing area contamination risk). Detection of the ECMs and pathogens are mutually exclusive.

Thus, in one embodiment, a method of controlling a multiplexed PCR system using a positive control material is disclosed herein. The method includes the steps of: providing an assay device comprising a first reaction chamber provided with a plurality of primers for multiplexed nucleic acid amplification, amplifying a plurality of positive control sequences in the first reaction chamber to yield a plurality of positive control amplicons, and detecting the positive control amplicons, wherein the positive control material does not contain a test sample. In one embodiment, not containing a test sample means that the positive control material contains no test organisms and no native sequences from test organisms. As described herein, control amplicons may be "derived" from test sequences insofar as the primer binding sites may have the same sequence as the test organism, but the sequence between the forward and reverse primers (e.g., the inner primers) of the positive control material may be wholly or partially synthetic or engineered to be different than and distinguishable from the native test sequence. In one aspect, detecting each of the positive control sequences (e.g., amplicons generated in the reaction from the positive control sequences) indicates that the multiplexed PCR system is operating correctly. In another aspect, each amplified positive control sequence melts at a different temperature from its corresponding test sequence as a result of the presence of the engineered sequences in the positive control sequences. In yet another aspect, melt signals for each of the amplified positive control sequences may be detected in the assay device or in a separate container.

In one embodiment, each positive control sequence includes an engineered sequence configured to minimize the likelihood that a false positive result will be observed. That is, the engineered sequence is different from and distinguishable from the native test sequence. So even if contamination and amplification from the positive control sequence(s) occurs, such contamination and amplification is readily distinguishable from the test sequence and will not result in a false positive result. In one embodiment, each positive control sequence and its corresponding test sequence have the same forward and reverse primer binding sites as the canonical sequence and wherein the engineered sequences are between forward and reverse primer binding sites. In one embodiment, the positive control material, which includes the positive control sequences, does not contain a test sample, a test sequence derived from a test sample, an organism (i.e., a test organism that the assay is designed to detect), or a test assay. That is, the positive control material is generally not run in the presence of test sequences or test organisms, although this may be done in some embodiments. In any case, because each amplified positive control sequence melts at a different temperature than its corresponding test sequence as a result of the presence of the engineered sequences in the positive control sequences, the positive control sequences should be readily distinguishable from test sequence amplicons. In one embodiment, the positive control sequence amplicons (aka ECM-specific amplicons) may melt in a melt window at a temperature in a range of about 2-14° C., 2-13° C., 2-12° C., 2-11° C., 2-10° C., 2-9° C., 2-8° C., 2-7° C., 2-6° C., 2-5° C., 2-4° C., 2-3° C., 3-14° C., 3-13° C., 3-12° C., 3-11° C., 3-10° C., 3-9° C., 3-8° C., 3-7° C., 3-6° C., 3-5° C., 3-4° C., 4-14° C., 4-13° C., 4-12° C., 4-11° C., 4-10° C., 4-9° C., 4-8° C., 4-7° C., 4-6° C., 4-5° C. or any combination thereof higher or lower than the Tm window of the corresponding test sequences.

In one embodiment, the amplifying step includes simultaneously amplifying 1-40 or more unique positive control sequences in the container, e.g., from about 2 to about 10, about 3 to about 20, about 4 to about 30, about 5 to about 40 positive control sequences, about 1 to about 40 positive control sequences, or any combination of the foregoing ranges. Because the positive control sequences are designed for multiplex amplification, one will appreciate that the engineered sequences are designed so that they do not cross-react with each other or with the primer sequences in reaction mixture. That is, the engineered sequences do not introduce new primer binding sites and the canonical forward and reverse outer and inner primer binding sites are the only primer binding sites in the reaction mixture. Likewise, the engineered sequences are designed so that they do not include regions of self-complementarity.

If the assays in the multiplexed nucleic acid amplification system are manufactured properly and the instruments and detection systems used to perform the amplification reactions are working correctly, then all positive control amplicons should be detected. Thus, in another embodiment, a method of detecting a plurality of primers within a multiplexed nucleic acid amplification system is disclosed. The method includes the steps of: providing a positive control material comprising a plurality of positive control sequences, providing a reaction container comprising the plurality of primers for amplification of each of the positive control sequences, amplifying the plurality of positive control sequences in the reaction container, wherein the positive control material does not contain a test sample (or the like), and detecting a melt signal for each amplified positive control sequence in the reaction container. Detecting a melt for each positive control sequence is positive confirmation that each of the primers that are supposed to be in the reaction are present. Thus, in one aspect, a melt signal of each of the plurality of positive control sequences indicates presence of each corresponding primer pair in the reaction container. In one embodiment, the plurality of positive control sequences are provided at a level near the limit of detection (LOD) of the assay. The pre-prepared positive control material, which is pre-mixed and pre-diluted to contain selected positive control sequences at selected concentrations can eliminate the need to dilute and combine many pathogens. Each positive control sequence provided includes an engineered sequence configured to minimize observing a false positive result relative to a corresponding test sequence. Each amplified positive control sequence melts at a different temperature from its corresponding test sequence as a result of the presence of the engineered sequence.

As in previous embodiments, each amplified positive control sequence melts at a different temperature from its corresponding test sequence as a result of the presence of the engineered sequence. Nevertheless, each positive control sequence and its corresponding test sequence comprise the same forward and reverse primer binding sites and wherein the engineered sequences are between forward and reverse primer binding sites. In one embodiment, the amplifying step includes simultaneously amplifying 1-40 or more positive control sequences in the reaction container, e.g., from about 2 to about 10, about 3 to about 20, about 4 to about 30, about 5 to about 40 positive control sequences, about 1 to about 40 positive control sequences, or any combination of the foregoing ranges.

In a similar embodiment, an assay device for a multiplexed nucleic acid amplification is disclosed. The assay device includes a first reaction chamber in the assay device provided with a plurality of primers for multiplex amplification of a plurality of positive control sequences, wherein each positive control sequence corresponds to a test sequence, and wherein each positive control sequence and each test sequence can be amplified in the first reaction chamber with the same primers. In one embodiment, the plurality of positive control sequences may be provided in the assay device, or they may be added to the assay device by a user at or near the time of use. Each positive control sequence includes an engineered sequence configured to minimize obtaining a false positive result from contamination by the positive control sequences. Each positive control sequence binds a different primer sequence of the plurality of primers within the first reaction chamber. While the assay device includes a plurality of primers for multiplex amplification of test sequences that correspond to the positive control sequences, the first reaction chamber does not contain a test sample. That is, the positive control sequences are typically intended to be run separately than a corresponding set of test sequences that may be derived from a test sample. However, one will appreciate that because the positive control sequences and the pathogen/test sequences are amplified with the same primers and they have melts that can be distinguished, the positive control and test sample could be run in the same multiplex reaction. However, one will appreciate that running the positive control and test sample in the same reaction may create primer competition between amplification of the positive controls and test samples. Nevertheless, running the positive controls and test samples in the same reaction may be used for PCR quantitation in a single reaction. For example, in any test sample there are likely to be some absent organisms. However, the positive control sequences that correspond to those absent organisms are present in the ECM and are added at a known concentration. Such positive controls should amplify at a known rate and with no primer competition. Thus, the positive control sequences that correspond to the absent organisms can be used as a reference for the efficiency of the PCR reaction and as a reference for the starting concentration of the template molecules in the reaction as a whole. Even if all of the organisms to be tested for are present, the positive control sequences can be used as a reference for the efficiency of the PCR reaction and as a reference for the starting concentration of the template molecules in the reaction as a whole because the positive control sequences are added at a known concentration. In one embodiment, the assay device further includes at least a second reaction chamber in the assay device fluidly connected to the first reaction chamber. The second reaction chamber includes primer pairs configured for further amplification of each of the positive control sequences and the corresponding test samples.

In one embodiment, a system is disclosed for multiplexed nucleic acid amplification that is configured to use the positive and negative control materials described herein. The system includes a positive control material that includes a plurality of positive control sequences that may be used as assay positives and a negative control material that may be used as a negative control for all assays, an assay apparatus including a first reaction chamber provided with a plurality of primers for multiplexed nucleic acid amplification of each of the positive control sequences (or for amplification of a corresponding set of test sequences), an instrument configured to receive the assay apparatus and to perform a nucleic acid amplification reaction to produce a plurality of positive control amplicons and to detect the positive control amplicons, and a software module for instructing the instrument to amplify the plurality of positive control sequences and to detect the positive control amplicons. In one embodiment, the software module may also instruct the instrument that the negative control material is being run and that no amplification of the positive control sequences or test sequences should be detected. The positive control sequences, when amplified with the primers included in the system, each have at least one detectable property that is different and distinct from at least one detectable property of each of a corresponding plurality of test sequences. In one embodiment, melting transitions of the positive control amplicons are distinct from melting transitions of test amplicons corresponding to each of the positive control amplicon. Each positive control sequence comprises an engineered sequence configured to minimize a false positive resulting from the positive control sequences, and each positive control sequence binds a different primer sequence of the plurality of primers within the assay device.

In one embodiment, the system may include a software module that may be configured to at least partially reprogram or repurpose the instrument to inform the instrument that a positive control material is being run in an assay device and that the positive control material is different than a test sample (e.g., a sample that includes one or more organisms or organism-derived nucleic acids that are normally detected in the assay device). For example, the software module may define a melt transition window for each amplicon derived from each of the positive control sequences that is different from and distinguishable from a positive amplicon window for each amplicon derived from test sequences that correspond to each of the positive control sequences. One of the advantages of the positive control sequences described herein is that positive control contamination can be tracked and distinguished from organism contamination. Thus, in another embodiment, the software module is configured to interrogate the melt transition window for each amplicon derived from each of the positive control sequences and the positive amplicon window for each amplicon derived from the test sequences to distinguish between positive control contamination and organism contamination. Likewise, the software module may be configured to at least partially reprogram or repurpose the instrument to inform the instrument that a negative control sample is being run and that a negative run is different than either the positive control material or the test sample. In general, the negative control sample should be negative for all amplicons from the positive control material and negative for the test sample sequences in order for the system to score a truly negative result.

In the forgoing embodiments, each positive control sequence in the positive control material (e.g., a pre-prepared ECM) comprises an engineered sequence configured to minimize the likelihood of observing a false positive result relative to a corresponding test sequence. Each positive control sequence binds a different primer sequence of the plurality of primers within the assay apparatus, nonspecific binding of the primers to the engineered sequence is minimized, and each positive control sequence has a melting temperature different from its corresponding test sequence—i.e., a higher temperature or a lower temperature as compared to each corresponding test sequence. In one embodiment, the foregoing positive control material may include 1-40 or more positive control sequences, e.g., from about 2 to about 10, about 3 to about 20, about 4 to about 30, about 5 to about 40 positive control sequences, about 1 to about 40 positive control sequences, or any combination of the foregoing ranges.

In one embodiment, the positive control material with the positive control sequences described herein includes two controls: one positive control mixture and one negative control mixture. As discussed previously, the positive control mixture is designed to detect the presence of all of the primers and reagents in the assay and to confirm that the assay and instrument are working according to specification. The negative control mixture is designed to confirm that the assay was not contaminated with any amplifiable sequence(s) at the time of manufacture and that it was not contaminated with positive control sequence(s) or test sequence(s) in the laboratory. In one embodiment, the negative control mixture may be essentially free of nucleic acids (i.e., no positive control sequences and no test sequences) but otherwise contain all of the components (buffers, salts, stabilizers, etc.) of the positive control mixture, or one or more of the components (i.e., the buffers, salts, stabilizers, etc.) may be omitted. In another embodiment, negative controls may be generated that contain non-amplifiable sequences that look similar to the positive controls. For example, the sequences of the primer binding sites in the negative controls may be jumbled or otherwise engineered so that they cannot be 'recognized' by the primers and, thus, cannot be amplified. In such a case, the ECM-specific sequence (5010 in FIG. 5) may be the same. Thus, while providing a true negative that cannot be amplified or detected in the systems described herein, such a negative control would be more similar to the actual test or positive control material in that the components of the reaction (e.g., buffers, primers, polymerases, etc.) are exposed to a negative control that is substantially similar to the positive control sequences or the test sequences. However, the negative control mixture may be any dried or liquid material (e.g., nucleic acid-free water), so long as it does not contain either the positive control sequences or the test sequences.

In one embodiment, the positive control mixture and the negative control mixture may each be provided in a single-use format to minimize the chances of cross-contamination. For example, the positive control mixture and the negative control mixture may each be provided in a dried form in, for example, a septum vial that can allow a user to rehydrate the positive control mixture and the negative control mixture in a manner that minimizes or eliminates cross contamination and that minimizes release of the positive control mixture or the negative control mixture after use. In one embodiment, the system may include a vial configured for delivering (e.g., injecting) a sample to the assay apparatus (e.g., a pouch). In one embodiment, the vial may be a single-use device that has the positive control sequences therein so that the positive control sequences can be delivered to the assay apparatus with minimal handling and manipulation by a user. In general, packaging the positive control material in a single-use format and minimizing handling and manipulation by the user significantly minimizes the risks of cross-contamination. Likewise, because the positive control materials may be dried, for example, in a septum vial, the positive control materials can be shipped and stored at ambient temperature in, for example, a humidity controlled package with little risk of breakdown. In one embodiment, the positive control materials are DNA templates, which are generally more stable relative to RNA templates.

While the term "vial" is used herein, one will appreciate that the positive control material may be provided to a user in other forms configured for delivering the positive control material into the assay apparatus without departing from the spirit of this disclosure. For example, the positive control material may be provided dried in or on a delivery device, such as a pipette, a swab, or another absorbent member that may be inserted into a fluid in a sample delivery component for injection into the assay apparatus. In another embodiment, the delivery device with a positive control material may be inserted directly into the assay apparatus. In one embodiment, the positive control material may be embedded in or on the delivery device in such a way as to minimize contamination upon transfer to the assay apparatus. In one embodiment, the positive control material is provided dried in or on the delivery device, thereby allowing for room-temperature storage. In a specific example, the positive control mixture and the negative control mixture may each be provided pre-packaged in a sample vial that may be configured for injecting a sample into a FilmArray pouch like pouch 510 of FIG. 1.

Figure 6A:
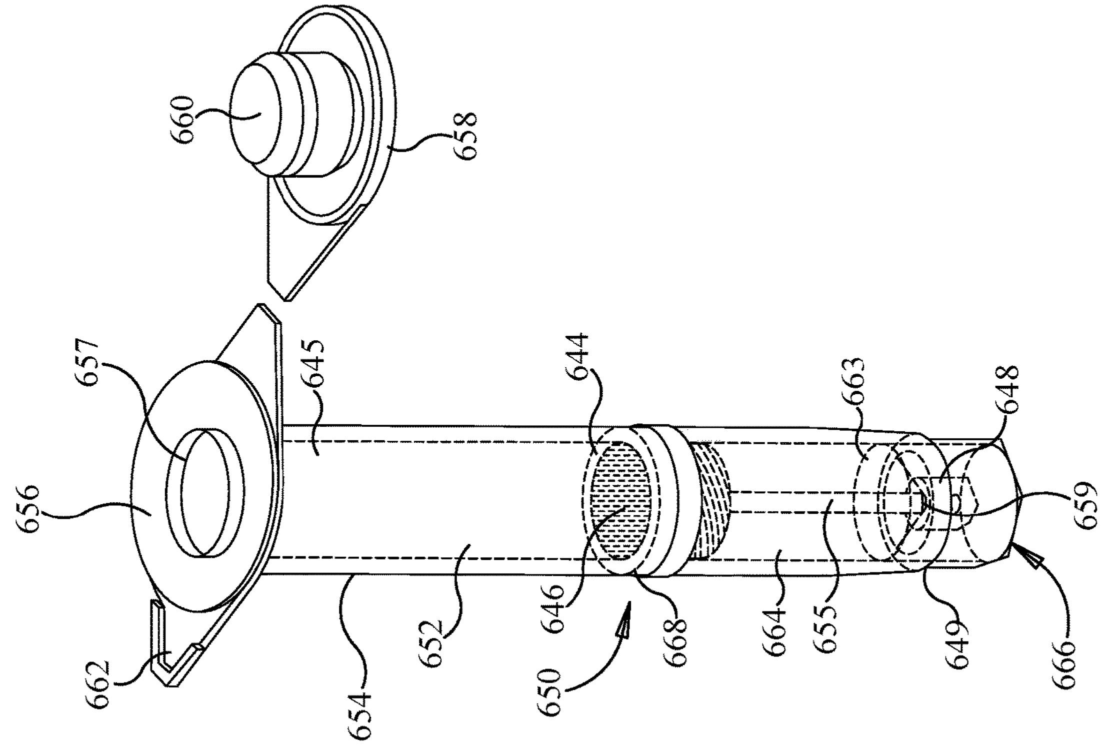
FIG. 6A shows a loading vial for loading a sample into the pouch of FIG. 1.
Figure 6B:
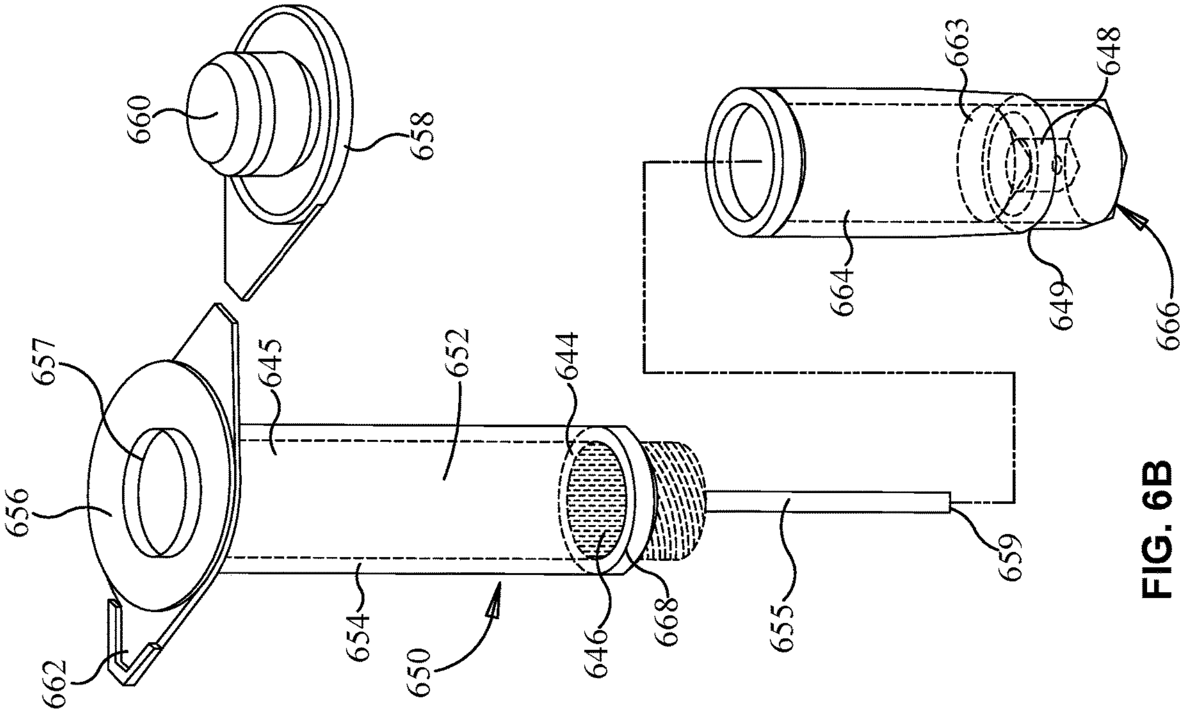
FIG. 6B shows an exploded view of the loading vial of FIG. 6A.

An illustrative sample vial 650 is shown in FIGS. 6A and 6B. Sample vial 650 is comprised of a top surface 662, a vial body 654, and a cannula 655, in an arrangement similar to many cannulated syringes. In this illustrative embodiment, rather than the plunger found in many cannulated syringes, sample vial 650 is provided with a seal 657 affixed to top surface 662 and a cap 658 for extending through top surface 662 for sealing body 654. In the illustrative embodiment, seal 657 is a peelable seal that can be peeled off by the operator. However, it is understood that the seal can be of a variety of different configurations, for example a screw cap or a frangible seal, as are known in the art. Alternatively, a separate seal may be omitted, and sample vial 650 may be provided with cap 658 closing vial body 654, thereby requiring the operator to open cap 658 prior to use. Additionally, a seal of any type is only required if sample vial 650 is provided pre-loaded with sample buffer or other fluid, or if vial body 654 needs to remain sealed from an outside environment prior to use, such as to maintain integrity of the positive or negative control mixtures. In an alternative embodiment, sample vial 650 may be provided empty, without seal 656, and the operator would pour, pipette, insert swab, scoop solid or semi-solid material, or otherwise transfer a fluid and/or other materials through opening 657 in top surface 662 and into vial body 654.

As shown, bottom cap 664 is provided with a hexagonal portion 666, which may be configured to configured to fit into a hexagonally shaped sample vial receptacle shown at 602 of FIG. 16 of U.S. Pat. Pub. No. 2014/0283945, which was already incorporated by reference in its entirety herein above. While portion 666 and sample vial receptacle are hexagonal in the illustrative embodiment, it is understood that other shapes may be used, and that the hexagonal or other mating or interlocking shapes may be provided to assist the operator in removing bottom cap 664. Alternatively, the operator may remove bottom cap 664 by other means, such as using two hands to twist bottom cap 664 from vial body 654. Bottom cap 664 may be press-fit on, threaded onto, or otherwise affixed to vial body 654.

In the illustrative embodiment, bottom cap 664 is provided with a seat 648, whereby a bottom end 659 of cannula 655 extends into seat 648. Illustratively, bottom end 659 of cannula 655 fits tightly into seat 648, such that seat 648 provides an airtight seal around the open bottom end 659 of cannula 655. Optionally, vents 649 are provided between bottom cap 664 and vial body 654.

In one embodiment, filter 646 may be, illustratively, located at or near the bottom surface 668 of vial body 654. Filter 646 may be held in place by an o-ring or a similar structure in the vicinity of 644. However, it is understood that filter 646 may be held in place by adhesive, by welding, by being press-fit into place, or by other means, as are known in the art. When cannula 655 is inserted into sample injection opening 663 and the sample is drawn into pouch 510, the sample material is filtered as it is pulled through filter 646 and into cannula 655. While the selection of filter material depends on the sample type and particle size, suitable filters for various biological samples include Pall 100 μm Absolute Ultipleat Polypropylene Melt Blown Media and Millipore 80 μm Polypropylene Net Filter. Most syringe filters are designed to exclude organisms of a certain size, thereby removing those organisms from the filtrate. Unlike such pre-existing filters, these illustrative filters were chosen based on their ability to exclude larger particulates found in stool, soil, powder, etc., while allowing target organisms (e.g., bacterial, viral, protozoan and fungal organisms) of approximately 60 μm in diameter or less to pass through the filter. Also, the illustrative filter material is inert (i.e. does not bind organism or nucleic acid) and is relatively resistant to clogging. It is understood that these illustrative filters were chosen for samples that include protozoans as target organisms (up to about 60 μm). Because some pouch configurations may test only for smaller targets, filters with a smaller pore size may be desired, such as filters with pore sizes of 1-10 μm for bacteria and fungi, and pore sizes of less than 1 μm if only viral particles are to be detected. Of course, the larger pore size filter can still be used to filter smaller targets. Such filters may be particularly useful for sample types that have a large amount of particulate matter, such as soil, stool, and powder that may clog the fluid system.

Further, it is understood that the pore size is chosen based on the materials to be filtered, and that other pore sizes are within the scope of this invention. Other non-limiting embodiments of injection vials may be found in U.S. Pat. Pub. No. 2014/0283945, which was already incorporated by reference in its entirety herein above.

When sample buffer or another fluid is added to sample vial 650 and the cannula 655 is inserted into sample injection opening 663 and the fluid is drawn into pouch 510, the positive or negative control mixtures in the sample vial 650 will be resuspended and drawn in with the fluid. In one embodiment, a kit may include positive and negative control mixtures. In one embodiment, each positive control mixture is a pool of synthetic DNA sequences that are capable of being amplified by the primers and reagents in the assay. In one embodiment, concentrations of the positive control sequences should approximate the lower range of clinically relevant levels for the assay system. In one embodiment, the positive control material may be processed in an assay device (e.g., pouch 510) in the same manner as a clinical sample. The use of room temperature stable positive controls contained within an injection vial simplifies and allows for more austere use of external controls relative to refrigerated and frozen liquid external control materials used with other FilmArray panels. Each individually packaged, ready-to-use positive or negative control mixture may be processed separately in a manner that closely mirrors the same process outlined for the processing of clinical samples. Each positive or negative control mixture is intended for a single use.

Accordingly, in one embodiment the present disclosure includes a positive control material that includes a cannulated injection vial (see, e.g., sample vial 650 as shown in FIGS. 6A and 6B). The cannulated injection vial includes a vial body having an interior volume for receiving a fluid, and a cannula extending away from an exterior of a bottom surface of the vial body, the cannula having a first end and a second end, the first end of the cannula adjacent to the bottom surface of the vial body, and a plurality of positive control sequences disposed in (e.g., dried on or in) the cannulated injection vial and configured to be resuspended when a fluid is added to the vial body. In another embodiment, the positive control material may be provided in a cannulated vial in a hydrated, ready-to-use format. Each of the positive control sequences comprises an engineered sequence configured to minimize occurrence of a false positive result, and wherein the collection vial does not contain a test sample. In one embodiment, the present disclosure may include a negative control material that is also provided in a cannulated vial. Several possible compositions for the negative control mixture are discussed in greater detail herein above.

In one embodiment, each positive control sequence has a melting temperature different from a corresponding test sequence. In one embodiment, each positive control sequence is engineered to melt at a higher temperature or a lower temperature than each test sequence that corresponds to each of the test sequences. In embodiments where each positive control sequence is melted in a separate well, such as but not limited to individual wells 582 of array 580 illustrated, for example, in FIGS. 1 and 3, it is understood that the positive control sequences do not need to have melt temperatures that are distinct from other positive control sequences that are melted in other wells.

In the foregoing positive control material, there may be 1-40 or more positive control sequences dried in the cannulated injection vial, e.g., about 2 to about 10, about 3 to about 20, about 4 to about 30, about 5 to about 40 positive control sequences, about 1 to about 40 positive control sequences, or any combination of the foregoing ranges.

In another embodiment, an external control kit is disclosed. The external control kit may include a sample collection device (e.g., a vial, a swab, or the like) having dried therein or thereon a positive control mixture that includes a plurality of positive control sequences, and a software module for programming an instrument to amplify the plurality of positive control sequences in a multiplexed assay system and to detect the positive control sequences as distinct from the corresponding test sequences. The positive control sequences may be provided in a dried form configured to be resuspended when a fluid is added to the sample collection device, or the positive control sequences may be provided in a hydrated, ready to use format. Each positive control sequence is engineered to melt at a higher temperature or a lower temperature than each corresponding test sequence. In one embodiment, the external control kit may also include a negative control mixture that is designed to be negative for both the positive control sequences and the corresponding test sequences when the negative control mixture is processed in the same manner as the positive control mixture. In one embodiment, the software module for programming the instrument may be configured to process the negative control in the same way as the positive control and to evaluate a negative result as being negative for both the positive control sequences and the corresponding test sequences.

In the foregoing external control kit, the positive control mixture may contain 1-40 or more positive control sequences, e.g., about 2 to about 10, about 3 to about 20, about 4 to about 30, about 5 to about 40 positive control sequences, about 1 to about 40 positive control sequences, or any combination of the foregoing ranges.

In one embodiment of the kit, the software module may be configured to at least partially reprogram or repurpose the instrument to inform the instrument that a positive control material is being run and that the positive control material is different than a test sample. For example, the software module may define a melt transition window for each amplicon derived from each of the positive control sequences that is different from and distinguishable from a positive amplicon window for each amplicon derived from test sequences that correspond to each of the positive control sequences. One of the advantages of the positive control sequences described herein is that positive control contamination can be detected differently than organism contamination or contamination from nucleic acids derived from the organisms and that positive control contamination can be tracked differently than organism contamination. Thus, in another embodiment, the software module is configured to interrogate the melt transition window for each amplicon derived from each of the positive control sequences and the positive amplicon window for each amplicon derived from the test sequences to distinguish between positive control contamination and results obtained or derived from organism. For instance, if a negative ECM sample is being run, the software module may instruct the instrument to interrogate the organism melt window and the shifted ECM melt window to identify and report on both ECM positive contamination and positive contamination obtained from organism. Thus, users can do their own risk analysis and respond to contamination appropriately. In one embodiment, the kit may include user instructions for performing an external control material validation.

Accordingly, embodiments of the present disclosure provide numerous advantages over existing systems.

Examples

The following Examples are intended to illustrate embodiments of the invention and are not intended to limit the scope of the description or the appended claims. For instance, while the following Examples refer specifically to the FilmArray system and specifically to the FilmArray Global Fever assay, one will appreciate that this is illustrative only and that the ECM concept described in this application and the Examples can be applied to other platforms and other molecular assays.

The applicant has developed a special type of positive controls (i.e., external control material (ECM)) as a quality control for the FilmArray Global Fever (GF) Panel (BioFire Defense, LLC), which is under development. These positive controls are being developed for at least two reasons: 1) to allow customers using the FilmArray Global Fever Panel to perform laboratory validations without having to obtain and test rare clinical specimens or analytes that require biosafety level 3 and 4 containment, and 2) to reduce the risk of false positive results that could result from contamination of a laboratory with traditional external control materials derived from the same pathogens assayed by the FilmArray GF Panel. Detection of the ECMs and pathogens are mutually exclusive in the FilmArray software analysis. In addition, the ECM positive controls are designed to be room-temperature stable, which eases manufacture, shipping, and storage, and the ECMs can be prepared for use with minimal manipulation and preparation by the user.

Background and Significance

The FilmArray Global Fever Panel is being developed to detect pathogens in samples from individuals with Acute Febrile Illness (AFI) to conduct 19 tests from whole blood specimens to identify pathogens that cause AFI (Table 1).

TABLE 1

Pathogens Detected by the FilmArray GF Panel

| Disease | Pathogen Assay Result | Type |
|---|---|---|
| Anthrax | *Bacillus anthracis* | Bacterial |
| Leptospirosis | *Leptospira* spp. | |
| Plague | *Yersinia pestis* | |
| Tularemia | *Francisella tularensis* | |
| Typhoid fever | *Salmonella enterica* serovar Typhi | |
| Paratyphoid fever | *Salmonella enterica* serovar Paratyphi A | |
| Malaria | *Plasmodium* spp. | Protozoan |
| | *Plasmodium falciparum* | |
| | *Plasmodium vivax/ovale* | |
| Leishmaniasis | *Leishmania* spp. | |
| Chikungunya fever | Chikungunya virus | Viral |
| Crimean-Congo Hemorrhagic Fever | Crimean-Congo hemorrhagic fever virus | |
| Dengue fever | Dengue virus | |
| Filoviruses | Ebola virus | |
| | Marburg virus | |
| Lassa fever | Lassa fever virus | |
| West Nile fever | West Nile virus | |
| Yellow fever | Yellow fever virus | |
| Zika fever | Zika virus | |

Quality controls are used to ensure proper performance of an IVD system. The ECMs, described here, are intended as laboratory quality controls to verify the presence of pathogen assay primers in the two PCR stages of the FilmArray GF Panel pouches. Positive controls will use synthetic DNA to be “Detected” for all assays contained on the GF Panel array. The negative control contains no nucleic acid and a successful run will be “Not Detected” for all assays on the panel. These controls are not intended to replace internal FilmArray Global Fever Panel pouch controls (process control and second-stage PCR array control).

The illustrative GF Panel Control Kit is designed to mitigate the risk of control contamination or misuse when evaluating clinical samples on the FilmArray System. Each positive ECM DNA sequence produces a signature melting temperature (Tm) value that is distinct from that produced by the corresponding pathogen amplicon. By design, even when contaminated, the positive GF Panel ECMs will not be detected when using the GF Panel whole blood protocol and reciprocally, amplified pathogen-specific nucleic acid would not be detected when using the positive control protocols. In one embodiment, the negative control protocol may, in a case of actual contamination, detect both pathogen amplicons and positive ECM controls. Thus, a positive detection when running a negative control protocol may provide the user with information regarding the source of the contamination. Through modification of the sequence between the inner primers for each ECM nucleic acid, the Tm value of the amplicon will be shifted to higher or lower Tm values (e.g., at least 2-6° C.) relative to the expected GF Panel target amplicon while running the same GF Panel pouches and the same protocol in the FilmArray instrument. The ECM specific pouch module software will detect the expected shifted Tm values as being from the primers and the ECM amplicons, thereby providing the necessary external positive controls to evaluate the performance of the FilmArray System. Also, the modification of the ECM sequence mitigates possible contamination events and would not cause false positives in clinical samples. In the unlikely event that an operator allows positive GF Panel ECM to contaminate a patient sample, the ECM sequence Tm values are not detected by the GF Panel whole blood pouch protocol, where different Tm windows are used to detect amplified pathogen sequence.

In this illustrative embodiment, the control kit may contain positive and negative controls, although it is understood that one or both of these controls may be provided, as desired. Each positive control is a pool of synthetic DNA targets reactive for the GF Panel primers that may be air-dried into a modified sample FilmArray Injection Vial (FAIV). Illustratively, ECM concentrations may approximate the lower range of assay LOD (e.g., 1-100×5-50×, preferably about 10× of the assay limit of detection (LOD)), although different levels may be used. As the ECM will be processed in a manner similar to processing for a clinical sample, users do not typically need to be retrained or specially trained to run an ECM. In this illustrative example, the use of room temperature stable dried ECMs contained within an injection vial simplifies and allows for more austere use of external controls relative to refrigerated and frozen liquid external control materials, although it is understood that refrigerated or frozen materials may be used, and such materials may be provided in an injection vial as described herein, or may be provided separately. Illustratively, each individually packaged ready-to-use control of FilmArray Global Fever (GF) Control Kit is processed separately and is intended for a single use. The user need only hydrate the positive control or the negative control, with minimal handling.

As discussed above, an example of a FilmArray Injection Vial 650 is illustrated in FIGS. 6A and 6B. The positive ECM controls may be dried in one vial, and the negative control may be provided as a second vial.

The Global Fever (GF) Panel Control Kit is illustratively provided for use as an external positive and negative assayed quality control to monitor the performance of in vitro laboratory nucleic acid testing procedures for the qualitative detection of *Bacillus anthracis, Francisella tularensis*, Leptospira spp., *Salmonella enterica* serovar Paratyphi A, *Salmonella enterica* serovar *Typhi, Yersinia pestis*, Chikungunya virus, Crimean-Congo hemorrhagic fever virus, Dengue virus (serotypes 1, 2, 3 and 4), Ebola virus, Lassa virus, Marburg virus, West Nile virus, Yellow fever virus, Zika virus, *Leishmania* spp., and *Plasmodium* spp. (including species differentiation of *Plasmodium falciparum, Plasmodium vivax*, and *Plasmodium ovale*) on the FilmArray Global Fever (GF) Panel performed on FilmArray 2.0 systems.

The Global Fever (GF) Panel Control Kit is a surrogate control material comprised of dried synthetic DNA in buffer and stabilizer, supplied in a dried form in a FilmArray Injection Vial that is used directly with the GF Panel. The GF Panel Control Kit may be composed of two control vials: a positive control vial and a negative control vial. The DNA in the positive control includes DNA segments to assess the presence of each individual assay in the FilmArray Global Fever (GF) Panel listed above. There may be no DNA in the negative control, or, in some embodiments, the negative control may contain DNA that cannot be amplified by the GF panel primers. In any case, the Global Fever (GF) Panel Control Kit contains no biological hazards and is 100% non-infectious.

FilmArray Global Fever System

The FilmArray Global Fever pouch is a disposable closed system that stores all the necessary reagents for sample preparation, reverse transcription, polymerase chain reaction (PCR), and detection in order to isolate, amplify, and detect nucleic acid from multiple pathogens within a single clinical whole blood specimen or from an external control material. The user injects hydration solution from one vial on one side of the pouch (similar to pouch 510 of FIG. 1) and either sample or external control material combined with sample buffer from another vial into the other side of the pouch. The user then places the pouch into a FilmArray instrument (similar to instrument 800 of FIG. 2), and starts an automated run.

During a run, the FilmArray system:

Lyses the sample by agitation (bead beading).

Extracts and purifies all nucleic acids from the sample using magnetic bead technology.

Performs nested multiplex PCR by:

First performing a single, large volume, highly multiplexed first-stage PCR reaction (PCR1).

Then performing multiple, singleplex, second-stage PCR reactions (PCR2) to amplify sequences within the PCR1 products.

Uses endpoint melting curve data to detect and generate a result for each target on the FilmArray Global Fever array.

Process Controls

Two process controls are included in each pouch:

1. RNA Process Control

The RNA Process Control assay targets a specific sequence in the *Schizosaccharomyces pombe* genome. *S. pombe* is freeze-dried into the sample injection port of each GF Panel pouch. When the sample is injected, the *S. pombe* is rehydrated and enters the pouch with the sample. *S. pombe* nucleic acid is extracted, purified, and tested along with the nucleic acid from the patient sample. A positive result for the RNA Process Control indicates that all processes (nucleic acid extraction, reverse transcription, PCR, and melt analysis) were completed successfully.

2. PCR2 Control

The PCR2 Control assay detects a DNA target that is dried into one or more wells of the array along with the corresponding primers. A positive result indicates that PCR2 was successful.

In this illustrative system, both control assays must be positive for the test run to pass. If the controls fail, the sample should be retested using a new pouch. For a valid run, these integrated controls must be positive when testing specimens and ECMs.

The illustrative external control kits described herein are separate from these process controls. It is understood that external control kits provided herein may be provided in addition to process controls.

Instrument Software

The instrument software has two primary functions. The first is to control the instrument and the second is to collect, view, store, and analyze test data. The illustrative software is comprised of the base software and panel-specific pouch modules that can be added without requiring an update to the core software. Pouch modules contain the panel-specific sample protocols, analysis, and reporting elements. Specific pouch modules are installed on the systems independent of the base software, such that the addition of new pouch modules can be accomplished without a change to the base software. This approach allows for flexibility in adding new reagent pouches to the system with negligible risk of interfering with previously released reagent pouches.

The illustrative Global Fever Panel pouch module may include three Global Fever Panel-specific sample protocols for selection by the operator. The "GF Blood" protocol is selected when testing a clinical blood specimen. The "GF Positive Control" protocol is selected when testing a Positive Control from the Global Fever (GF) Panel Control Kit, and the optional "GF Negative Control" protocol is selected when testing a Negative Control. In the negative control, all detections should be negative except for the RNA process control and the PCR2 control, which are designed to be positive in every FilmArray pouch. To detect possible contamination derived from ECM or test organisms in the negative controls, the negative control protocol may be designed to interrogate both the shifted ECM melt windows and the corresponding organism melt windows. Thus, contamination and its source (ECM or organism/test amplicon) can be detected, if present, and users can perform their own risk analysis. However, it is understood that a single control protocol may be used for running the positive and negative controls, with the negative controls only outputting a negative result in the positive control melt window. Each of these sample protocols physically manipulates the Global Fever Panel pouch identically. The Tm data analysis is different for the control protocols, and interpretation of an ECM test is performed automatically by the software, providing an external control Passed or Failed result. The risk of confusing a control run with a clinical sample run will be mitigated through specific results page labeling and a separate control kit.

FilmArray Global Fever (GF) Panel Control Kit

The FilmArray Global Fever (GF) Control Kit contains surrogate control material comprised of synthetic DNA segments. The positive and negative controls may be provided in a Film Array Injection Vial (FAIV) or in another easy to use, single-use format (e.g., provided wet or dried in a septum vial such that the controls can be rehydrated with addition of aqueous media through the septum and, likewise, extracted without contamination through the septum), or may be provided separately for loading into a GF pouch. The positive control is manufactured by diluting and suspending purified synthetic DNA in a non-infectious solution of buffers and stabilizers, which may be provided dried in the FAIV. Each positive control DNA segment contains sequence that is recognized and amplified by the inner and outer primers specific for one Global Fever Panel assay, plus approximately 25 base pairs of pathogen sequence on either side of the outer primer sequence. In addition, the original pathogen sequence inside the two innermost primer recognition sites of each positive control DNA segment has been replaced with a synthetic sequence (i.e., the ECM insert) that alters the denaturation characteristics (Tm) of the inner amplicon.

In the case of the Global Fever panel, it was found that the pathogen sequences inside the two innermost primer recognition sites could be replaced with one of several sequences. As discussed elsewhere herein, the ECM inserts were designed initially by identifying sequences with minimal or no cross-reaction between the inserts and the panel primer sets, and then sequences were identified that resulted in higher or lower melting points. For example, an amplicon with an already high melting point may have its inner primer sequence replaced with a low-melt insert in order to generate an ECM amplicon with a lowered melting point outside the test sequence melt window. Similarly, an amplicon with an already low melting point may have its inner primer sequence replaced with a high-melt insert in order to generate an ECM amplicon with a raised melting point outside the test sequence melt window.

As a consequence of the design process, each of the positive control DNA segments is amplified by one set of Global Fever Panel assay primers (some GF Panel analytes are interrogated by multiple assays, requiring multiple DNA segments to fully test for the presence of all primers associated with that analyte), but is not detected within the target temperature melt window. The negative control may contain no buffers, stabilizers, nucleic acids, etc., or the negative control may be prepared by drying the same non-infectious solution of buffers and stabilizers without DNA in the FAIV. The FilmArray Global Fever (GF) Panel Control Kit can be safely handled in accordance with biosafety level 1 practices.

Control Materials for Customer Validation

Clinical diagnostic laboratories are generally required by accrediting agencies to perform a verification of new tests prior to offering the test for clinical use. For FDA-cleared tests, the laboratory must verify that system performance is consistent with that described by the manufacturer. In addition, laboratories are also required to verify the performance of each new operator and lot and/or shipment of reagent test kits prior to using them in clinical testing. These verification tests are typically performed with well-characterized clinical samples or commercially available organism stocks. For tests that detect rare or select agents, limited availability of test material can be an obstacle to completing an appropriate verification of the test system.

The positive and negative control materials composed of synthetic target nucleic acids discussed herein can be used to verify performance of various tests, such as the Global Fever Panel assays. In the illustrative example, external control material is designed to amplify in the Global Fever Panel pouch, creating amplicons with a characteristic and different Tm, as compared to the amplicons from GF Panel analytes. When an operator wishes to run a positive or negative control, the positive or negative (respectively) control sample protocol is selected, rather than the blood sample protocol. The control sample protocols are similar to the blood sample protocols in that all pouch manipulation is identical, but the software analyzes the data using different Tm windows. Thus Global Fever Panel positive controls will only pass when the correct positive control module is selected, and will not result in false positive diagnostic results. Similarly, a Global Fever Panel clinical specimen will result in a failed run if the positive control module is selected. This will greatly reduce the risk of false positives due to contamination with positive control materials. While reference is made to the FilmArray Global Fever Panel, it is understood that similar tests could be used as control materials for other single-plex and multiplex assays and on platforms other than the FilmArray system.

For example, FIGS. 7A and 7B illustrate amplification (FIG. 7A) and melting-based detection of an amplicon from Crimean-Congo hemorrhagic fever virus (CCHF) within the target window (FIG. 7B), leading to a positive test result. In contrast, FIGS. 7C and 7D illustrate amplification (FIG. 7C) and melting (FIG. 7D) of synthetic CCHF1 external control material (ECM). CCHF1 ECM will amplify (FIG. 7C) but melt outside the target window for the test amplicon (FIG. 7D), leading to a negative test result. FIG. 7E illustrates a melt similar to 7D, except the detection window is shifted to the ECM-specific melt window to yield a positive ECM result.

Figure 8:
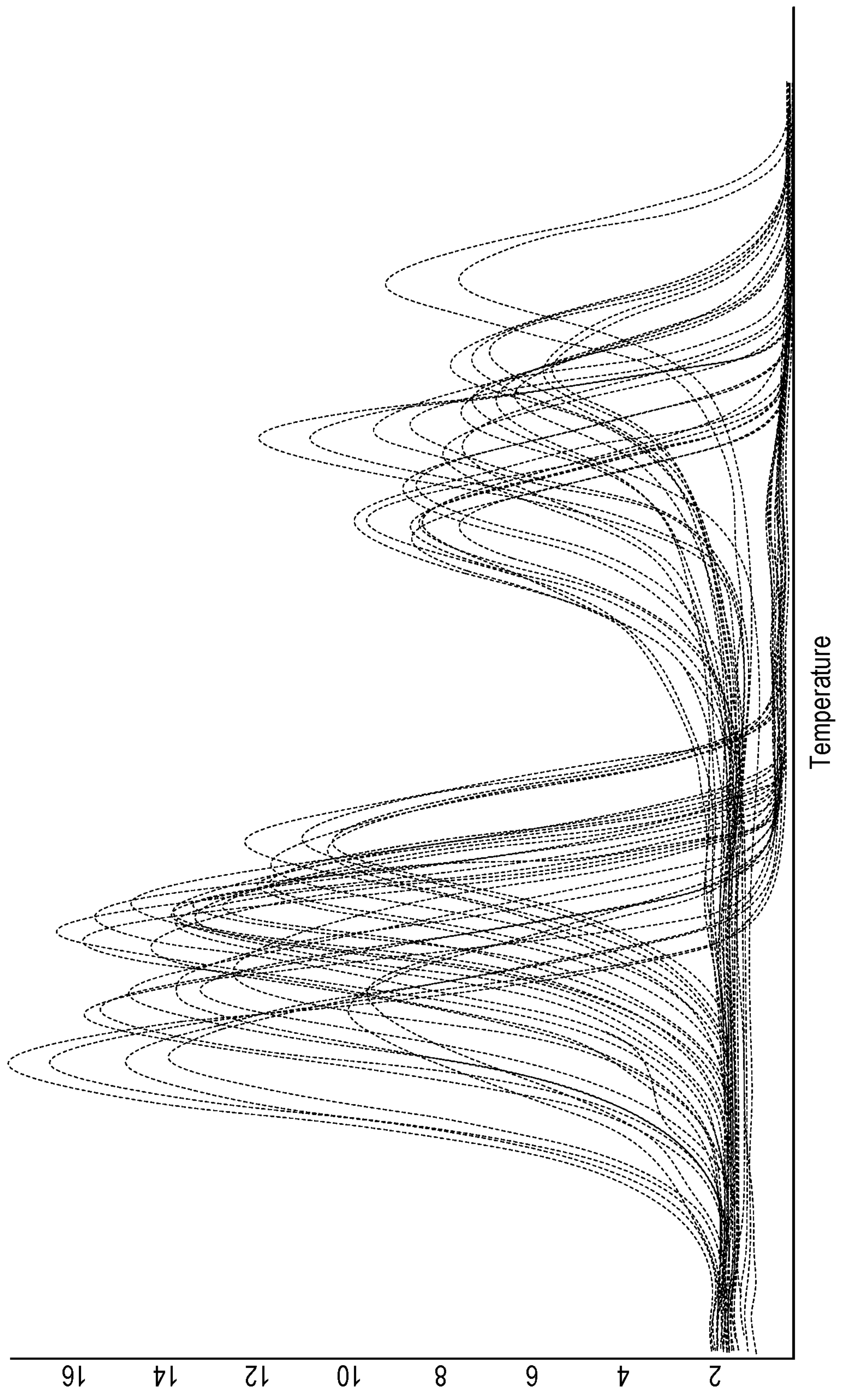
FIG. 8 illustrates melting of a multiplexed ECM mix; the ECM mix was amplified in a first-stage and second-stage multiplex format and melted in a pouch similar to the pouch illustrated in FIG. 1.
Figure 9:
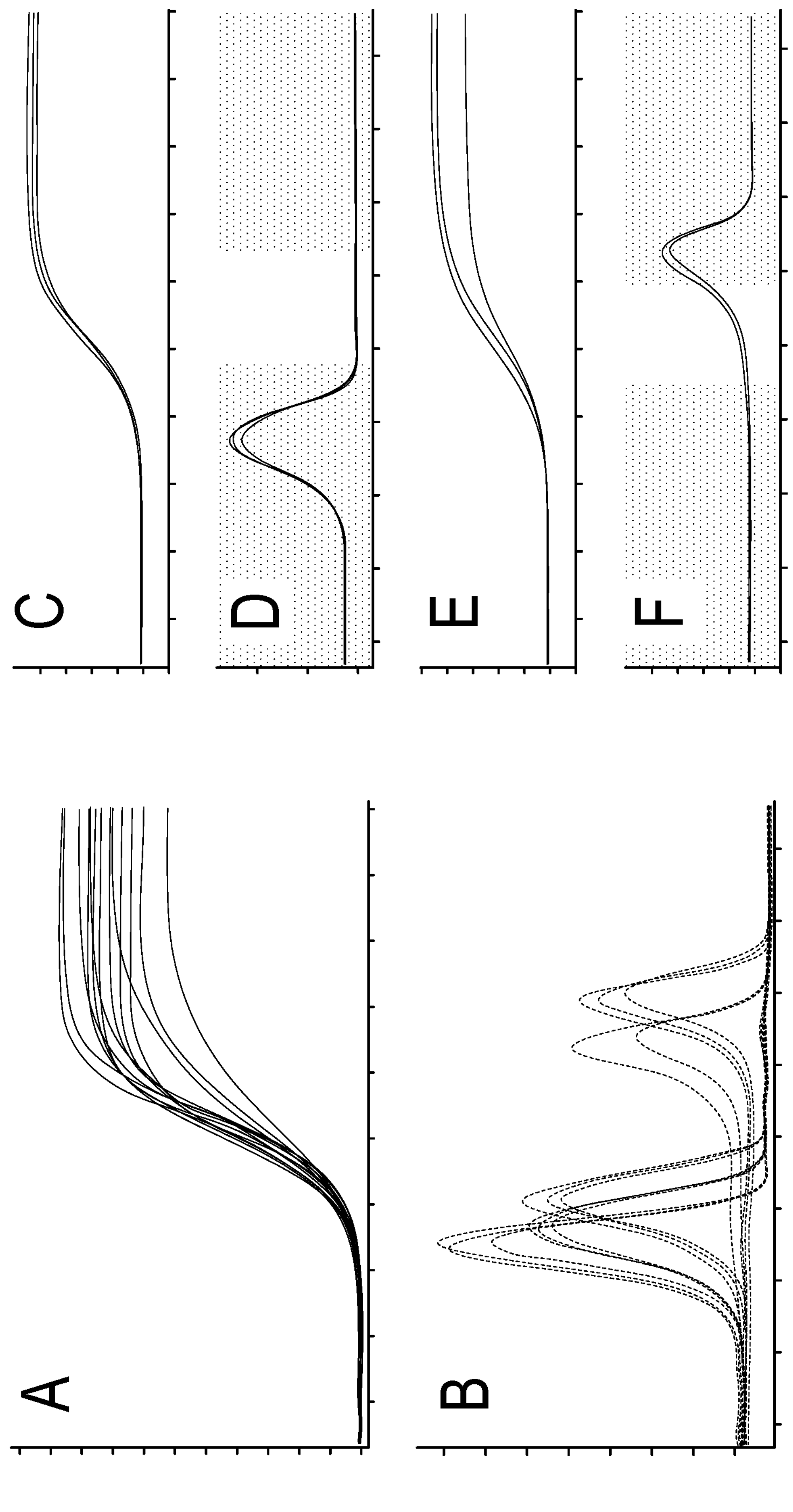
FIGS. 9A and 9B illustrate amplification and amplicon melting of a multiplexed ECM mix in a pouch similar to the pouch illustrated in FIG. 1.
FIGS. 9C and 9D and 9E and 9F illustrate amplification curves and melting curves for individual amplicons of the ECM mix of FIGS. 9A and 9B with the melts (FIGS. 9D and 9F) for the ECM amplicons appearing outside of the expected melt windows for the corresponding native sequences.

FIG. 8 illustrates the results of amplification and melting of the entire GF ECM mix, which includes approximately 40 amplicons. As can be seen in FIG. 8, some of the amplicons have melting peaks at or below 78° C. while other have melting peaks at or above 84° C. All have melting peaks shifted at least 2° C. (e.g., +/−2 to 6° C.) from the target Tm, either higher or lower. FIGS. 9A and 9B illustrate amplification (FIG. 9A) and melting (FIG. 9B) of ECMs for Dengue virus 1, Dengue virus 2.1, Dengue virus 2.2, Dengue virus 3, and Dengue virus 4. FIGS. 9C-9F illustrate amplification (FIGS. 9C and 9E) and melting (FIGS. 9D and 9F) of ECM amplicons for two of the Dengue assays, both outside their respective expected melt windows.

ECMs provide a procedure that allows laboratories to test the Global Fever Panel to satisfy laboratory verification requirements in a time and resource efficient manner, while minimizing potential for contamination. Laboratories may use the ECMs for initial laboratory verification of systems such as the FilmArray GF Panel system. In addition, evaluation with external controls is recommended prior to using a new shipment or new lot of kits, when there is a new operator, and following replacement or major preventive maintenance of a system.

In addition to the foregoing, the Global Fever (GF) panel is designed to detect multiple variants of some viruses. Because co-detection of these variants is unexpected, primers specific for these variants may be co-spotted in single wells of the second stage array and still allow detection of the targets. The combined assays in the GF panel are:

| | |
|---|---|
| Ebola Bundi + Ebola Tai Forest | Ebola 1 |
| Ebola Reston + Ebola Sudan | Ebola 2 |
| Plas Vivax + Plas Ovale | Plas Vivax/Ovale |

Figure 10A:
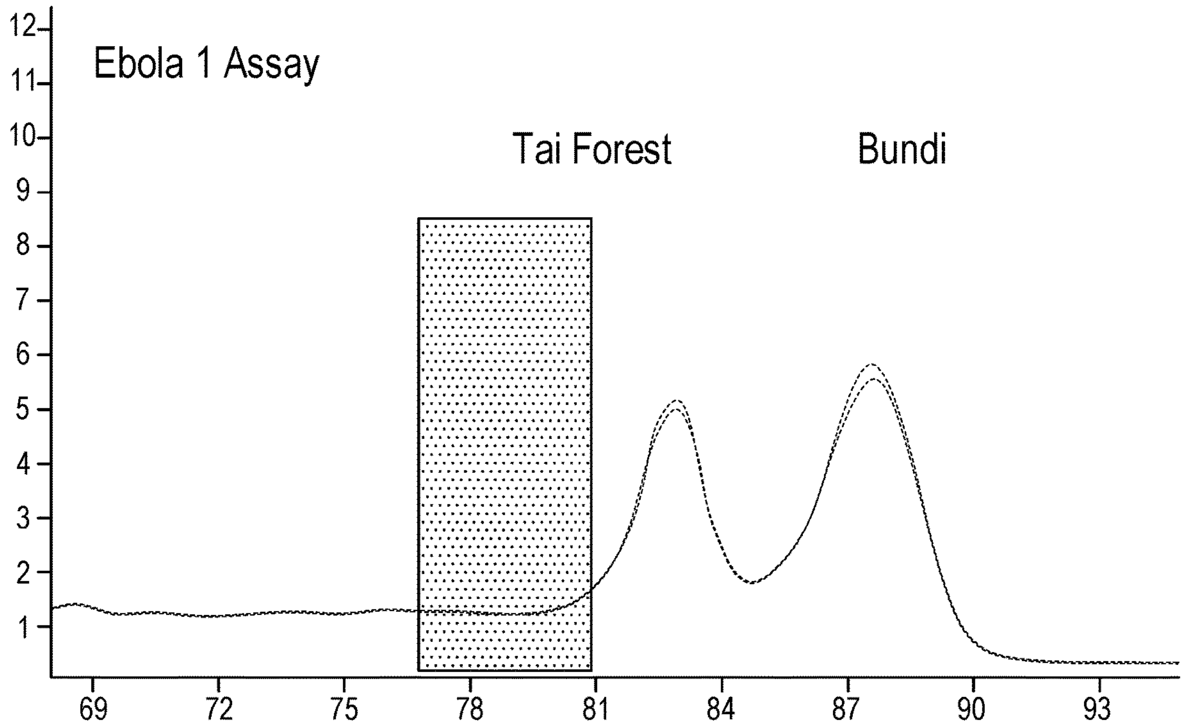
FIGS. 10A and 10B illustrate melting curves for ECM amplicons for ECM for multiple strains of Ebola virus; in a pouch similar to the pouch of FIG. 1, the second stage wells configured for detection of Ebola include primer sets for amplification of two Ebola strains, with the ECM melts being distinguishable from one another and outside the expected melt windows.

For internal quality control, multiple quality control mixes for the multi-spotted wells can be split and tested independently. Alternatively, the primers in the multi-spotted wells may be detected with one ECM mix by using two templates that are melt shifted from the amplicons so that they are outside the expected melt windows and are distinct from one another. FIG. 10A illustrates exemplary melting curves for the ECM amplicons in the Ebola 1 assay and FIG.

Figure 10B:
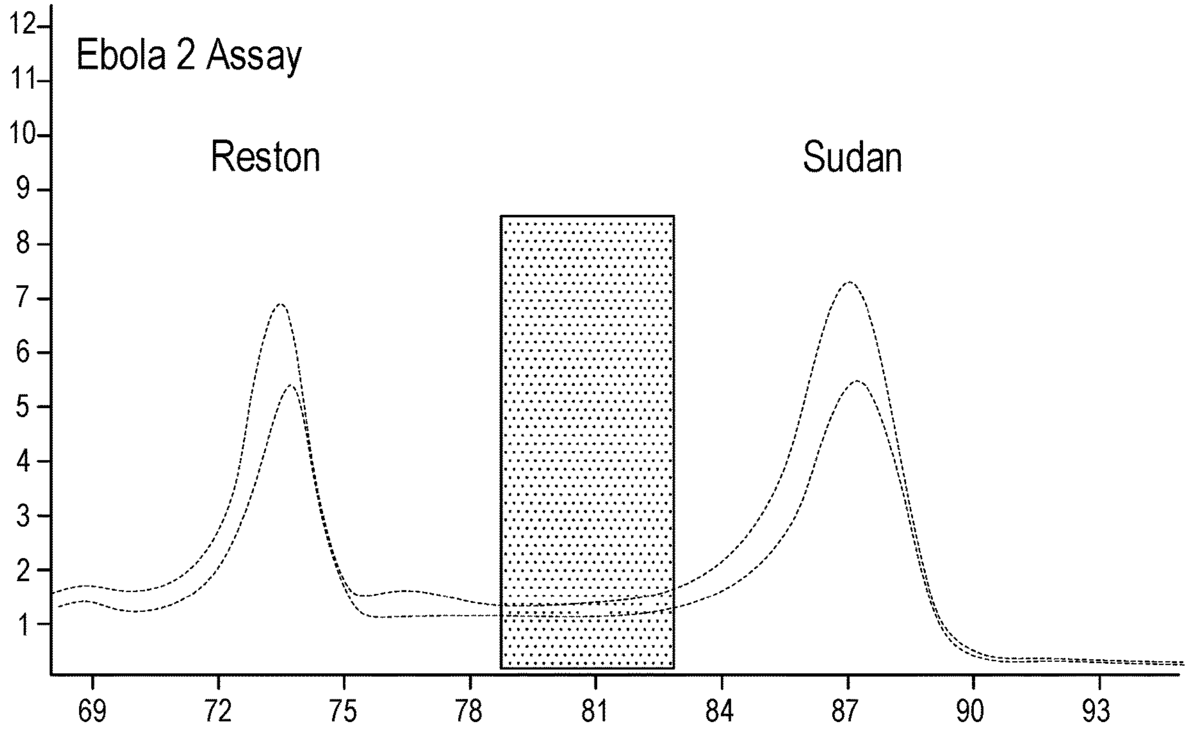
Figure 11:
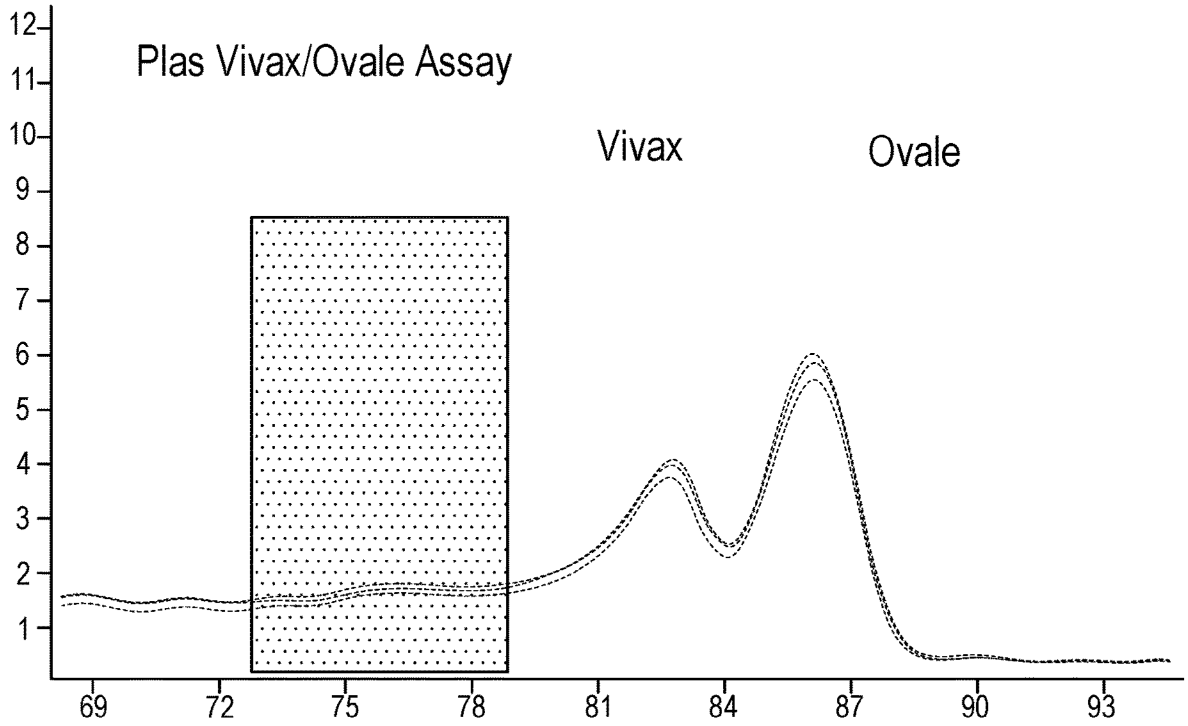
FIG. 11 illustrates melting curves for ECM amplicons for ECM for *Plasmodium vivax* and *Plasmodium ovale*; in a pouch similar to the pouch of FIG. 1, the second stage wells configured for detection of *Plasmodium* spp. include primer sets for amplification of two *Plasmodium vivax* and *Plasmodium ovale*, with the ECM melts being distinguishable from one another and outside the expected melt window.

10B illustrates exemplary melting curves for the ECM amplicons in the Ebola 2 assay. As can be seen, the melts are distinguishable and are outside the target melt window (grey boxes). It is noted that both external control templates that are tested together may be shifted in the same direction (FIG. 10A), or one may be shifted to a temperature lower than the target and the other shifted to a temperature higher than the target (FIG. 10B), provided that both templates have a melt that is distinguishable from each other and distinguishable from the pathogen targets. It is understood that while two templates are shown as multiplexed, more templates may be used, limited only by the resolution of the system for distinguishing different melts. Similarly, FIG. 11 illustrates melting curves for the ECM amplicons in the Plas Vivax/Ovale assay. As can be seen, the melts are distinguishable and outside the melt window (grey boxes).

Positive Control Levels

In one approach to capture variations in the system (reagents, instruments, operators, and environment), effective quality controls are used that approach the Limit of Detection (LoD) of the monitored assay but not so close to LoD that false negatives may occur, contributing to delayed patient result reporting and/or time spent needlessly troubleshooting. Control and pouch lot variability may be considered as the control concentration is finalized to minimize false negative results. Previous data suggests that crossing point values (Cps) of 18-20 cycles represent approximately 10× the LoD for the FilmArray Global Fever Panel assays.

CONCLUSION

While the foregoing detailed description makes reference to specific exemplary embodiments, the present disclosure may be embodied in other specific forms without departing from its spirit or essential characteristics. Accordingly, the described embodiments are to be considered in all respects only as illustrative and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the invention as defined by the appended claims. While reference is made to the FilmArray system and the Global Fever Panel, this is illustrative only, and external control materials as described herein may be developed for other systems.

The limitations recited in the claims are to be interpreted broadly based on the language employed in the claims and not limited to specific examples described in the foregoing detailed description, which examples are to be construed as non-exclusive and non-exhaustive. All changes which come within the meaning and range of equivalency of the claims are to be embraced within their scope.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment. In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein.

What is claimed is:

1. A method of quality control of a multiplexed PCR system using a positive control material comprising the steps of:

providing the positive control material comprising a plurality of positive control sequences corresponding to a plurality of test sequences, providing an assay device comprising a first reaction chamber provided with a plurality of primers for multiplexed nucleic acid amplification of the plurality of positive control sequences, wherein each positive control sequence comprises the same forward and reverse primer binding sites as its corresponding test sequence and an engineered sequence between the forward and reverse primer binding sites that is different than its corresponding test sequence, introducing the positive control material into the assay device, wherein the introducing does not include introducing a test sequence with the positive control material into the assay device, amplifying the plurality of positive control sequences in the first reaction chamber with the plurality of primers to yield a plurality of positive control amplicons, detecting the positive control amplicons, melting each positive control amplicon, and verifying by melting that each amplified positive control amplicon represents a positive control sequence, wherein detecting each of the positive control amplicons indicates that the multiplexed PCR system is operating correctly, and wherein each amplified positive control sequence has a melting temperature that is detectably different and distinct from a melting temperature of its corresponding test sequence as a result of the engineered sequence in each positive control sequence between the forward and reverse primer binding sites, and wherein each positive control sequence melts in a melt window at a temperature in a range of about 2-10° C. higher or lower than a melt window of its corresponding test sequence.

2. The method of claim 1, wherein each positive control sequence melts in a melt window at a temperature in a range of about 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melt window of its corresponding test sequence.

3. The method of claim 1, wherein the amplifying step includes simultaneously amplifying from about 10 to about 20, about 10 to about 30, or about 10 to about 40 unique positive control sequences in the assay device, and wherein each of the amplified positive control sequences has a melting temperature that is detectably different and distinct from the other amplified positive control sequences.

4. The method of claim 1, the assay device further comprising at least a second reaction chamber fluidly connected to the first reaction chamber, the second reaction chamber comprising primer pairs configured for further amplification of each of the positive control sequences, and wherein the method further comprises further amplifying the positive control sequences, wherein the further amplifying step occurs prior to the detecting step.

5. The method of claim 4, wherein the second reaction chamber includes an array of wells with each well having at least one primer pair therein for further amplification of each of the positive control sequences.

6. The method of claim 1, wherein detecting the positive control amplicons includes observing a DNA melting signal for each of the positive control amplicons, wherein the DNA melting signal is at the different temperature as compared to the melting temperatures of the test sequences that correspond to each positive control amplicon.

7. A method of quality control of a multiplexed PCR system using a positive control material comprising the steps of:

providing an assay device comprising a first reaction chamber provided with a plurality of primers for multiplexed nucleic acid amplification, providing a positive control material comprising a plurality of control sequences configured to be amplified by the plurality of primers, wherein each one of the plurality of control sequences comprises a same forward and a same reverse primer binding site as a corresponding test nucleic acid sequence and an engineered sequence between the forward and reverse primer binding sites that is different than the corresponding test nucleic acid sequence, wherein the plurality of control sequences control for amplification of one of more of Anthrax, Leptospirosis, Plague (*Yersinia pestis*), Tularemia, Typhoid fever, Paratyphoid fever, Malaria, Leishmaniasis, Chikungunya fever, Crimean-Congo Hemorrhagic Fever, Dengue fever, Ebola virus, Marburg virus, Lassa fever, West Nile fever, Yellow fever, or Zika fever, introducing the positive control material into the assay device, amplifying the plurality of positive control sequences in the first reaction chamber with the plurality of primers to yield a plurality of positive control amplicons, and detecting the positive control amplicons, melting each positive control amplicon, and verifying by melting that each amplified positive control amplicon represents a positive control sequence, wherein detecting each of the positive control amplicons indicates that the multiplexed PCR system is operating correctly, and wherein each amplified positive control sequence has a melting temperature that is detectably different and distinct from a melting temperature of each corresponding test sequence as a result of the engineered sequence in each positive control sequence between the forward and reverse primer binding sites.

8. The method of claim 7, wherein each positive control sequence melts in a melt window at a temperature in a range of about 2-10° C., 2-9° C., 2-8° C., 2-7° C., 2-6° C., 2-5° C., 2-4° C., 2-3° C., 3-10° C., 3-9° C., 3-8° C., 3-7° C., 3-6° C., 3-5° C., 3-4° C., 4-10° C., 4-9° C., 4-8° C., 4-7° C., 4-6° C., 4-5° C. or any combination thereof higher or lower than a melt window of its corresponding test sequence.

9. The method of claim 7, wherein the amplifying step includes simultaneously amplifying from about 2 to about 10, about 2 to about 20, about 2 to about 30, or about 2 to about 40 unique positive control sequences in the assay device, and wherein each of the amplified positive control sequences has a melting temperature that is detectably different and distinct from the other amplified positive control sequences.

10. The method of claim 7, the assay device further comprising at least a second reaction chamber fluidly connected to the first reaction chamber, the second reaction chamber comprising primer pairs configured for further amplification of each of the positive control sequences, and wherein the method further comprises further amplifying the positive control sequences, wherein the further amplifying step occurs prior to the detecting step.

11. The method of claim 10, wherein the second reaction chamber includes an array of wells with each well having at least one primer pair therein for further amplification of each of the positive control sequences.

12. The method of claim 7, wherein detecting the positive control amplicons includes observing a DNA melting signal for each of the positive control amplicons, wherein the DNA melting signal is at the different temperature as compared to the melting temperatures of the test sequences that correspond to each positive control amplicon.

* * * * *